US010209185B2

(12) United States Patent
Koudelka et al.

(10) Patent No.: US 10,209,185 B2
(45) Date of Patent: Feb. 19, 2019

(54) INTERFACE DETECTOR FOR BLOOD PROCESSING SYSTEM

(71) Applicant: Fenwal, Inc., Lake Zurich, IL (US)

(72) Inventors: Peter David Koudelka, St. Paul, MN (US); Ryan Eliot Eckman, Columbus, MN (US); Eric Karl Lindmark, Shoreview, MN (US); Lubomir Koudelka, Shoreview, MN (US); James Joseph Ulmes, Lake Zurich, IL (US); Steven R. Katz, Deerfield, IL (US); William H. Cork, Mettawa, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 15/414,717

(22) Filed: Jan. 25, 2017

(65) Prior Publication Data
US 2017/0131203 A1  May 11, 2017

Related U.S. Application Data

(62) Division of application No. 14/422,188, filed as application No. PCT/US2013/031494 on Mar. 14, 2013, now Pat. No. 9,594,020.
(Continued)

(51) Int. Cl.
G01N 33/48 (2006.01)
G01N 21/55 (2014.01)
(Continued)

(52) U.S. Cl.
CPC ........... *G01N 21/55* (2013.01); *A61M 1/3693* (2013.01); *B04B 13/00* (2013.01); *G01N 21/59* (2013.01);
(Continued)

(58) Field of Classification Search
CPC ...... G01J 1/0407; G01J 1/0411; G01J 1/0437; G01J 1/4228; G01J 1/4257; H01S 3/09415; H01S 3/0014
(Continued)

(56) References Cited

U.S. PATENT DOCUMENTS 3,727,066 A   4/1973   Louderback et al.
3,752,995 A   8/1973   Leidholz
(Continued)

FOREIGN PATENT DOCUMENTS

EP   0 342 730 A2   11/1989
WO   2006071302 A2   7/2006

OTHER PUBLICATIONS

International Search Report and Written Opinion for PCT Patent Appl'n. No. PCT/US2013/031494, dated Dec. 19, 2013.

*Primary Examiner* — Md M Rahman
(74) *Attorney, Agent, or Firm* — Cook Alex Ltd.

(57) ABSTRACT

Blood separation systems and methods are provided for controlling the interface between separated blood components. The system includes a centrifuge assembly having a light-transmissive portion, a light reflector, and a fluid processing region therebetween. An optical sensor system emits a scanning light beam along a path toward the light-transmissive portion, which transmits at least a portion of the scanning light beam to the fluid processing region and the light reflector. The light reflector reflects at least a portion of the scanning light beam toward the optical sensor system along a path substantially coaxial to the path of the scanning light beam from the optical sensor system toward the light-transmissive portion of the centrifuge assembly. The scanning light beam may be a white light beam or narrow spectrum beam. The reflected beam may be directed through the optical sensor system via optical fibers.

7 Claims, 18 Drawing Sheets

Related U.S. Application Data

(60) Provisional application No. 61/696,343, filed on Sep. 4, 2012.

(51) Int. Cl.
*A61M 1/36* (2006.01)
*G01N 21/59* (2006.01)
*B04B 13/00* (2006.01)
*G01N 33/49* (2006.01)

(52) U.S. Cl.
CPC ....... *G01N 21/5907* (2013.01); *G01N 33/491* (2013.01); *A61M 2202/0415* (2013.01); *A61M 2202/0427* (2013.01); *A61M 2202/0429* (2013.01); *A61M 2205/3306* (2013.01); *B04B 2013/006* (2013.01); *G01N 2201/062* (2013.01); *G01N 2201/0612* (2013.01); *G01N 2201/0636* (2013.01); *G01N 2201/08* (2013.01)

(58) Field of Classification Search
USPC .......................................................... 356/39
See application file for complete search history.

(56) References Cited

U.S. PATENT DOCUMENTS

| | | | |
|---|---|---|---|
| 3,778,171 A | 12/1973 | Chervenka | |
| 4,409,820 A | 10/1983 | Nash | |
| 4,468,219 A | 8/1984 | George et al. | |
| 4,557,719 A | 12/1985 | Neumann et al. | |
| 4,604,086 A | 8/1986 | Benko et al. | |
| 4,810,090 A | 3/1989 | Boucher et al. | |
| 5,104,526 A | 4/1992 | Brown et al. | |
| 5,316,666 A | 5/1994 | Brown et al. | |
| 5,316,667 A | 5/1994 | Brown et al. | |
| 5,400,261 A | 3/1995 | Reynolds | |
| 5,437,598 A | 8/1995 | Antwiler | |
| 5,570,697 A | 11/1996 | Walker et al. | |
| 5,573,678 A | 11/1996 | Brown et al. | |
| 5,592,402 A | 1/1997 | Beebe et al. | |
| 5,605,842 A | 2/1997 | Langley et al. | |
| 5,611,997 A | 3/1997 | Langley et al. | |
| 5,628,915 A | 5/1997 | Brown et al. | |
| 5,632,893 A | 5/1997 | Brown et al. | |
| 5,639,382 A | 6/1997 | Brown | |
| 5,656,163 A | 8/1997 | Brown | |
| 5,868,696 A | 2/1999 | Giesler et al. | |
| 5,948,271 A | 9/1999 | Wardwell et al. | |
| 5,958,250 A | 9/1999 | Brown et al. | |
| 5,961,842 A | 10/1999 | Min et al. | |
| 5,980,757 A | 11/1999 | Brown et al. | |
| 5,980,760 A | 11/1999 | Min et al. | |
| 6,063,292 A | 5/2000 | Leung | |
| 6,254,784 B1 | 7/2001 | Nayak et al. | |
| 6,312,607 B1 | 11/2001 | Brown et al. | |
| 6,899,666 B2 | 5/2005 | Brown | |
| 2004/0133086 A1 | 7/2004 | Ciurczak | |
| 2007/0239033 A1 | 10/2007 | Tearney | |
| 2008/0045394 A1* | 2/2008 | Kolenbrander | B04B 5/0442 494/7 |
| 2009/0073456 A1 | 3/2009 | Wax | |
| 2009/0087191 A1* | 4/2009 | Leard | G01J 3/02 398/152 |
| 2009/0129976 A1 | 5/2009 | Hoshino et al. | |
| 2009/0279902 A1* | 11/2009 | Granot | H04B 10/677 398/208 |
| 2012/0170020 A1 | 7/2012 | Bado et al. | |
| 2012/0190945 A1 | 7/2012 | Yamanaka | |
| 2014/0008277 A1 | 1/2014 | Foley | |
| 2014/0030729 A1* | 1/2014 | Basiji | G01N 33/57492 435/6.14 |
| 2015/0219558 A1 | 8/2015 | Koudelka et al. | |

* cited by examiner

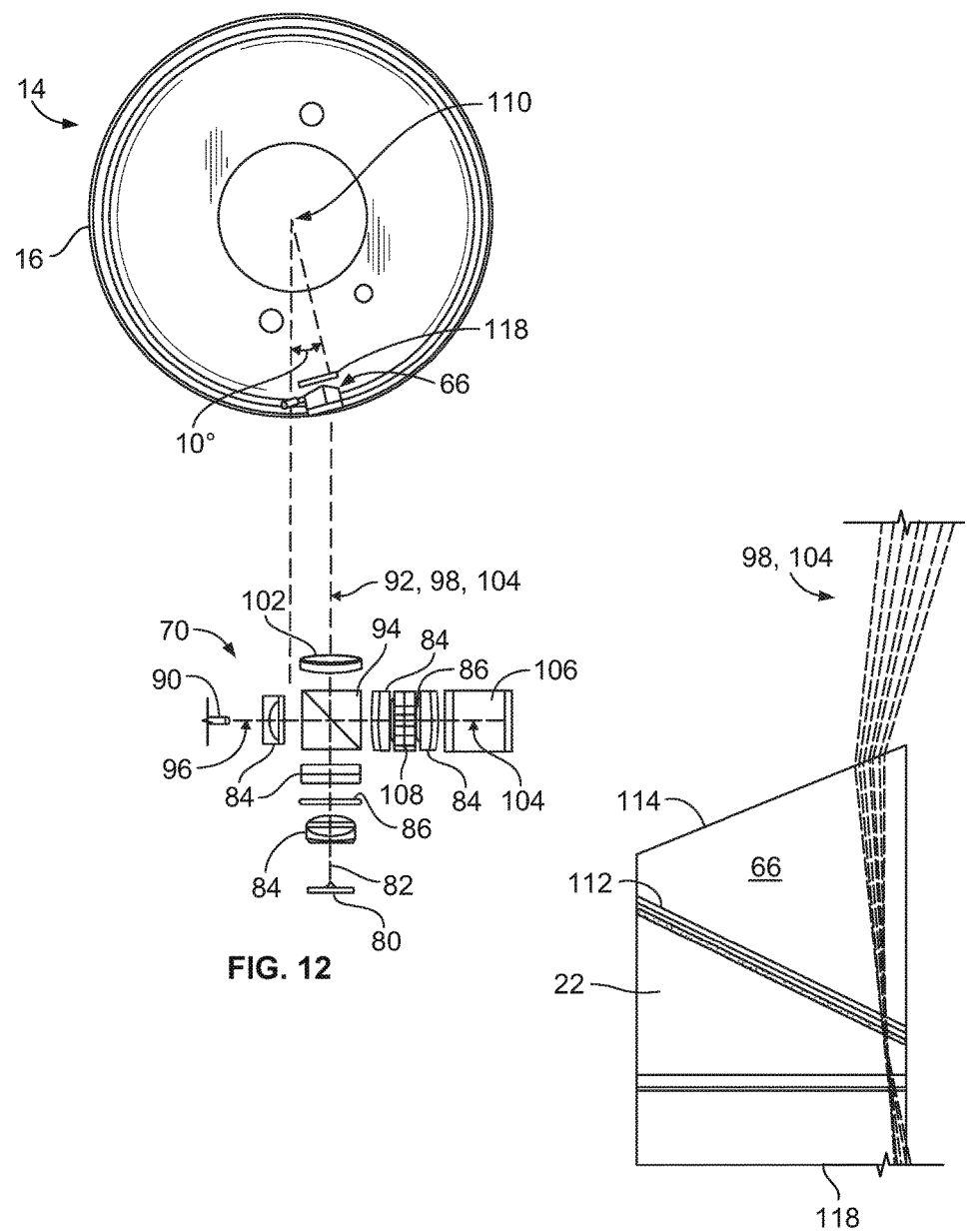

INTERFACE DETECTOR FOR BLOOD PROCESSING SYSTEM

RELATED APPLICATION

This application is a divisional of U.S. patent application Ser. No. 14/422,188, filed Feb. 18, 2015, which is a U.S national stage application of PCT Patent Application No. PCT/US13/31494, filed Mar. 14, 2013, which claims the benefit of and priority of U.S. Provisional Patent Application Ser. No. 61/696,343, filed Sep. 4, 2012, the contents of each of the above applications being incorporated by reference herein.

DESCRIPTION

Technical Field

The disclosure relates to blood treatment systems and methods. More particularly, the disclosure relates to systems and methods for optically detecting or monitoring characteristics of fluid (e.g., the location of an interface between separated blood components) within a centrifugal blood processing device.

BACKGROUND

Various blood processing systems now make it possible to collect particular blood constituents, instead of whole blood, from a blood source. Typically, in such systems, whole blood is drawn from a blood source, the particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents through centrifugation. This requires that the whole blood be passed through a centrifuge after it is withdrawn from, and before it is returned to, the blood source. To reduce contamination and possible infection (if the blood source is a human donor or patient), the blood is preferably processed within a sealed, sterile fluid flow system during the centrifugation process. Typical blood processing systems include a disposable, sealed, and sterile flow circuit, including a centrifuge chamber portion, that is mounted in cooperation on a durable, reusable assembly containing the hardware (centrifuge, drive system, pumps, valve actuators, programmable controller, and the like) that rotates a centrifuge chamber and controls the flow through the fluid circuit.

The centrifuge rotates the centrifuge chamber of the disposable flow circuit during processing. As the centrifuge chamber is rotated by the centrifuge, the heavier (greater specific gravity) components of the whole blood in the centrifuge chamber, such as red blood cells, move radially outwardly away from the center of rotation toward the outer or "high-G" wall of the centrifuge chamber. The lighter (lower specific gravity) components, such as plasma, migrate toward the inner or "low-G" wall of the centrifuge chamber. The boundary that forms between the denser red blood cells and the lighter plasma in the centrifuge chamber is commonly referred to as the interface. Various ones of these components can be selectively removed from the whole blood by providing appropriately located channeling structures and outlet ports in the flow circuit. For example, in one blood separation procedure, plasma is separated from cellular blood components and collected, with the cellular blood components and a replacement fluid being returned to the blood source. Alternatively, red blood cells may be harvested from the centrifuge chamber and the rest of the blood constituents returned to the donor. Other processes are also possible including, without limitation, platelet collection, red blood cell exchanges, plasma exchanges, etc. In these procedures, the efficiency of the process is often dependent upon accurate identification and control of the position of the interface during centrifugation.

It is known to employ an optical sensor system to monitor the flow of blood and/or blood components through the flow circuit in the centrifuge and determine various characteristics of the flow. For example, U.S. Pat. No. 6,899,666 to Brown relates to an optical sensor system for viewing into the centrifuge chamber for detecting and controlling the location of an interface between separated blood components in a centrifuge. While this system functions satisfactorily, there remains an opportunity to provide optical monitoring systems with improved interface detection and greater robustness.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a blood processing system includes a centrifuge assembly having a light-transmissive portion, a light reflector, and a fluid processing region at least partially positioned between the light-transmissive portion and the light reflector. The blood processing system also includes an optical sensor system configured to emit a scanning light beam along a path toward the light-transmissive portion of the centrifuge assembly. The light-transmissive portion of the centrifuge is configured to transmit at least a portion of the scanning light beam to the fluid processing region and the light reflector. The light reflector is configured to reflect at least a portion of the scanning light beam toward the optical sensor system along a path substantially coaxial to the path of the scanning light beam from the optical sensor system toward the light-transmissive portion of the centrifuge assembly.

In another aspect, a method is provided for monitoring fluid within a blood processing system having a centrifuge assembly. The method includes separating blood in a centrifuge assembly into at least two blood components and directing a scanning light beam along a path toward and into the centrifuge assembly so as to intersect the blood or at least one of the blood components. At least a portion of the scanning light beam is reflected after intersecting the blood or blood component, with the reflected light being directed along a path out of the centrifuge assembly that is substantially coaxial to the path of the scanning light beam toward and into the centrifuge assembly. At least a portion of the reflected light is received and analyzed.

In yet another aspect, an optical sensor system is provided for use in combination with a blood processing system. The optical sensor system includes a light source, a light detector, and an optical fiber providing a light path between the light source and the light detector.

In another aspect, a blood processing system includes a centrifuge assembly having a light-transmissive portion, a light reflector, and a fluid processing region at least partially positioned between the light-transmissive portion and the light reflector. The blood processing system also includes an optical sensor system having a light source configured to emit a source light beam, a light detector, and an optical fiber providing a light path to the light detector. The light-transmissive portion of the centrifuge assembly is configured to transmit at least a portion of the source light beam to the fluid processing region and the light reflector. The light reflector is configured to reflect at least a portion of the source light beam toward the optical sensor assembly. The optical fiber is configured to conduct at least a portion of the reflected source light beam toward the light detector.

In yet another aspect, a method is provided for monitoring fluid within a blood processing system having a centrifuge assembly. The method includes separating blood in a centrifuge assembly into at least two blood components and generating a source light beam. At least a portion of the source light beam is directed into the centrifuge assembly so as to intersect the blood or at least one of the blood components. At least a portion of the source light beam is reflected after intersecting the blood or blood component and is then directed toward a light detector through an optical fiber.

In another aspect, an optical sensor system for use in combination with a blood processing system includes a white light source.

In yet another aspect, a blood processing system includes a centrifuge assembly having a light-transmissive portion and a fluid processing region positioned at least partially adjacent to the light-transmissive portion. The blood processing system also includes an optical sensor system having a light source that emits a white light directed toward the light-transmissive portion of the centrifuge assembly.

In another aspect, a method is provided for monitoring fluid within a blood processing system having a centrifuge assembly. The method includes separating blood in a centrifuge assembly into at least two blood components and generating a source light beam comprising a white light. At least a portion of the source light beam is directed toward and into the centrifuge assembly so as to intersect the blood or at least one of the blood components. At least a portion of the source light beam is reflected after intersecting the blood or blood component and at least one characteristic of the reflected source light beam is detected.

In yet another aspect, a blood processing system includes a centrifuge assembly having a light-transmissive portion, a light reflector, and a fluid processing region at least partially positioned between the light-transmissive portion and the light reflector. The blood processing system also includes an optical sensor system having a light source configured to emit a source light beam and a plurality of light detectors. The light-transmissive portion of the centrifuge assembly is configured to transmit at least a portion of the source light beam to the fluid processing region and the light reflector. The light reflector is configured to reflect at least a portion of the source light beam toward the optical sensor system. The plurality of light detectors are configured to detect at least one characteristic of the reflected source light beam at different locations.

In another aspect, a method is provided for monitoring fluid within a blood processing system having a centrifuge assembly. The method includes separating blood in a centrifuge assembly into at least two blood components and generating a source light beam. The source light beam is directed toward and into the centrifuge assembly so as to intersect the blood or at least one of the blood components. At least a portion of the source light beam is reflected after intersecting the blood or blood component and at least one characteristic of the reflected source light beam is detected at a plurality of different locations.

In yet another aspect, a blood processing system includes a centrifuge assembly having a rotational axis. The blood processing system also includes an optical sensor system having a light source that emits a source light beam directed along a path parallel to a radius passing through the rotational axis of the centrifuge assembly. The path of the source light beam is oriented so as to not pass through the rotational axis of the centrifuge assembly.

In another aspect, a method is provided for monitoring fluid within a blood processing system having a centrifuge assembly with a rotational axis. The method includes separating blood in a centrifuge assembly into at least two blood components and generating a source light beam. At least a portion of the source light beam is directed along a path parallel to a radius passing through the rotational axis of the centrifuge assembly, but oriented so as to not pass through the rotational axis of the centrifuge assembly, and into the centrifuge assembly so as to intersect the blood or at least one of the blood components. At least a portion of the source light beam is reflected after intersecting the blood or blood component and then at least one characteristic of the reflected source light beam is detected.

In yet another aspect, a blood processing system includes a centrifuge assembly having a rotational axis. The centrifuge assembly has a light-transmissive portion, a fluid processing region positioned radially inwardly of the light-transmissive portion, and a yoke including a first support arm configured to rotate the light-transmissive portion and the fluid processing region about the rotational axis. The blood processing system also includes an optical sensor system configured to direct a light toward the light-transmissive portion of the centrifuge assembly. The yoke is positioned between the light-transmissive portion and the optical sensor system and is configured to allow passage of at least a portion of the light through the first support arm as the light is directed toward the light-transmissive portion.

In another aspect, a blood processing system includes a centrifuge assembly having a rotational axis. The centrifuge assembly has a light-transmissive portion, a fluid processing region positioned radially inwardly of the light-transmissive portion, and a yoke. The yoke includes a first support arm configured to rotate the light-transmissive portion and the fluid processing region about the rotational axis. An optical fiber bundle extends between first and second ends and is associated with the support arm of the yoke. The blood processing system also includes an optical sensor system configured to direct a light toward the first end of the optical fiber bundle. The second end of the optical fiber bundle directs the light toward the light-transmissive portion.

BRIEF DESCRIPTION OF THE DRAWINGS

FIG. 12 is a top plan view of the bowl and optical sensor system or assembly of FIG. 8, with a housing or case of the optical sensor system omitted for illustrative purposes;

FIGS. 13 and 14 illustrate a light beam from the optical sensor system of FIG. 8 passing through the interface ramp of the centrifuge bowl and a centrifuge container or other fluid passage containing blood or blood components;

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
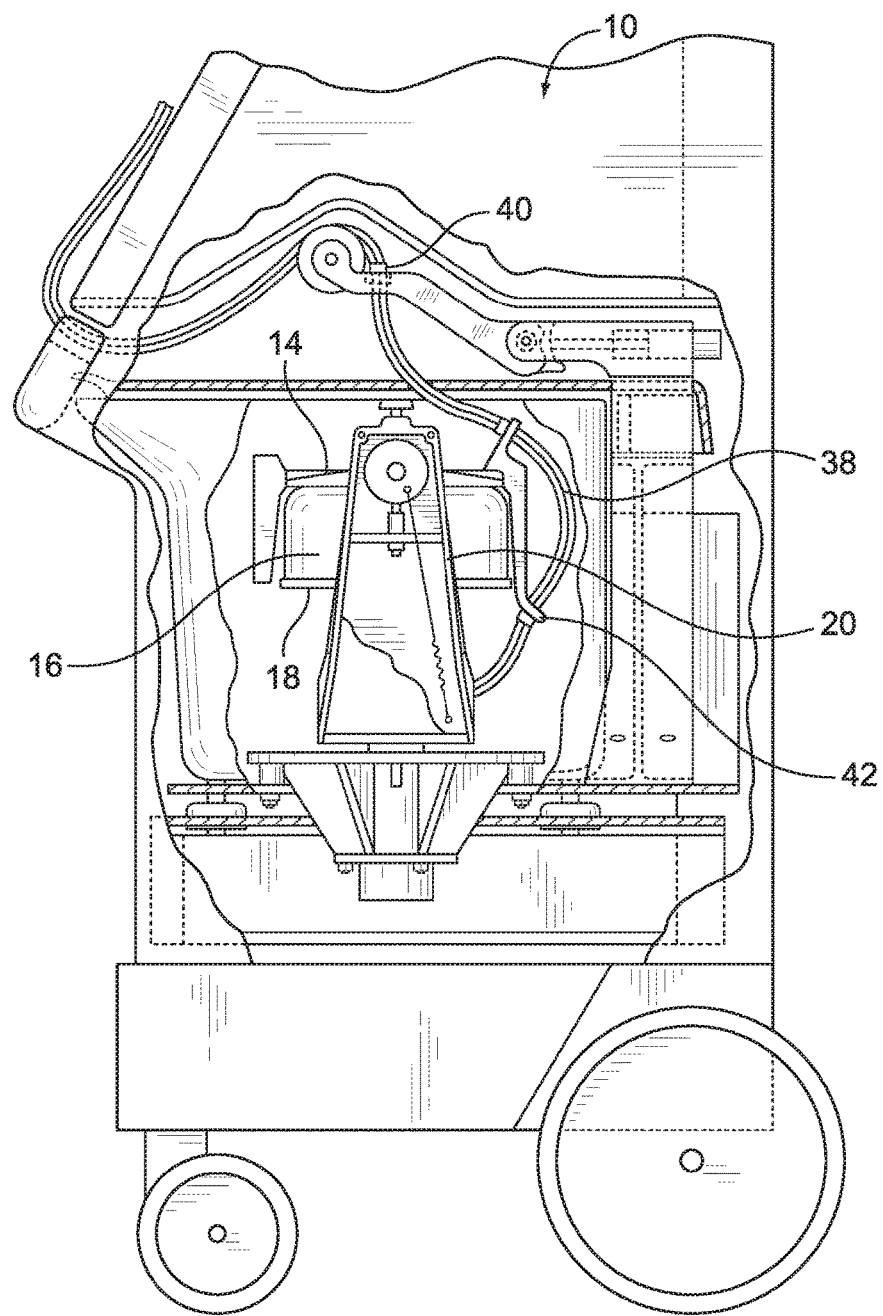
FIG. 1 is a side elevation view, with portions broken away and in section, of one example of a blood separation system employing aspects of the present invention, with a centrifuge bowl and spool of the system being shown in their operating position.
Figure 2:
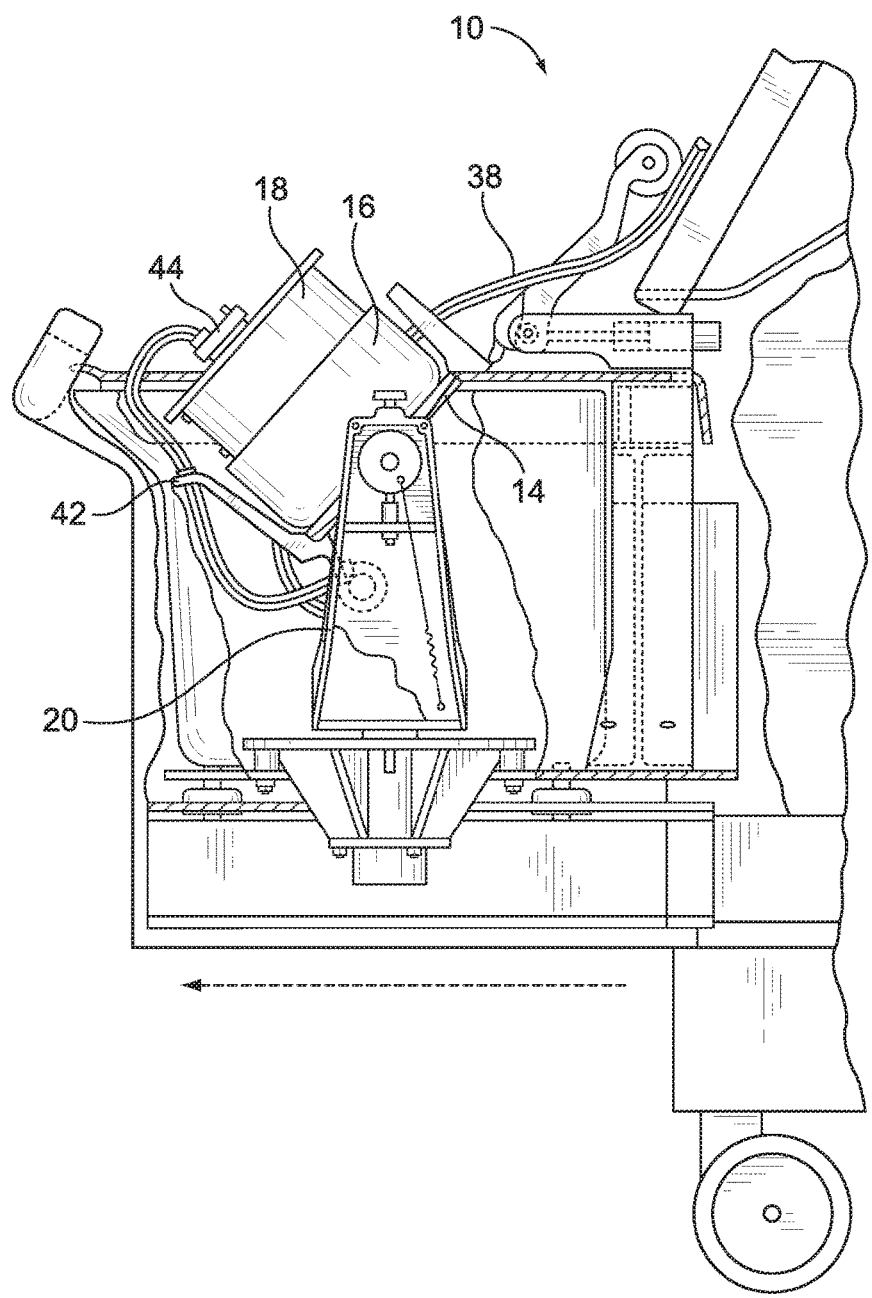
FIG. 2 is a side elevation view, with portions broken away and in section, of the system shown in FIG. 1, with the bowl and spool shown in an upright position for receiving a blood separation chamber.

FIGS. 1 and 2 show a centrifugal blood processing system 10 with an interface controller 12 (FIG. 16) having improved interface detection capabilities. The illustrated system 10 shares many centrifuge design aspects with a system currently marketed as the AMICUS® separator by Fenwal, Inc. of Lake Zurich, Ill., which is an affiliate of Fresenius Kabi AG of Bad Homburg, Germany, as described in greater detail in U.S. Pat. No. 5,868,696, which is hereby incorporated herein by reference. The system 10 can be used for processing various fluids, but is particularly well suited for processing whole blood, blood components, or other suspensions of biological cellular materials.

While interface control and optical detection principles will be described herein with reference to one particular system 10 and centrifuge assembly 14, it should be understood that these principles may be employed with other fluid processing systems (e.g., other centrifugal blood separation systems and centrifuges) without departing from the scope of the present disclosure.

A. The Centrifuge Assembly

The system 10 includes a centrifuge assembly 14 used to centrifugally separate blood components. The system 10 may be programmed to separate blood into a variety of components (e.g., platelet concentrate, platelet-rich plasma, and red cells). It may be used for platelet collection, therapeutic plasma exchange, red cell exchange, red cell or plasma collection, or other blood processing applications. For illustrative purposes only, a platelet collection procedure and a therapeutic plasma exchange procedure will be described herein. However, the principles described and claimed herein may be employed with other blood separation procedures without departing from the scope of the present disclosure.

The illustrated centrifuge assembly 14 shares certain design aspects with the one shown in U.S. Pat. No. 5,316,667 to Brown et al., which is incorporated herein by reference. The illustrated centrifuge assembly, which is shown for purposes of illustration and not limitation, comprises a bowl 16 and a spool 18. In one embodiment, the bowl 16 and spool 18 are pivoted on a yoke 20 between an operating position (FIG. 1) and a loading/unloading position (FIG. 2). Other methods of accessing the bowl 16 and the spool 18 may also be employed without departing from the scope of the present disclosure. The present subject matter may be used with centrifuges that do not employ such a spool and bowl, such as molded centrifuge chambers, centrifuge bowls with pre-formed processing chamber slots, or other designs.

When in the loading/unloading position, the spool 18 can be opened by movement at least partially out of the bowl 16, as FIG. 2 shows. In this position, the operator wraps a flexible blood separation chamber 22 (see FIG. 3) about the spool 18. Closure of the spool 18 and bowl 16 encloses the chamber 22 between the inner surface of the bowl 16 and the outer surface of the spool 18 (which collectively define the fluid processing region in which the chamber 22 is received) for processing. When closed, the spool 18 and bowl 16 are pivoted into the operating position of FIG. 1 for rotation about a rotational axis.

B. The Blood Separation Chamber

Figure 4:
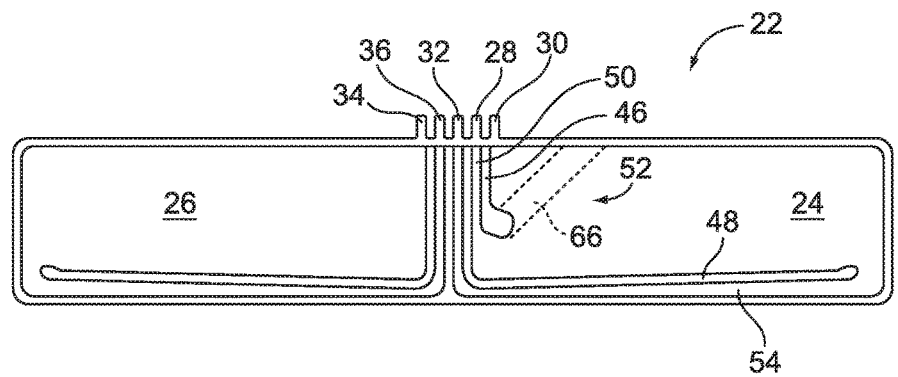
FIG. 4 is a plan view of the blood separation chamber shown in FIG. 3, out of association with the spool.

The blood separation chamber 22 can be variously constructed. FIG. 4 shows a representative embodiment.

The chamber 22 shown in FIG. 4 allows for either single- or multi-stage processing. When used for multi-stage processing of whole blood, a first stage 24 separates whole blood into first and second components. Depending on the nature of the separation procedure, one of the components may be transferred into a second stage 26 for further processing.

Figure 3:
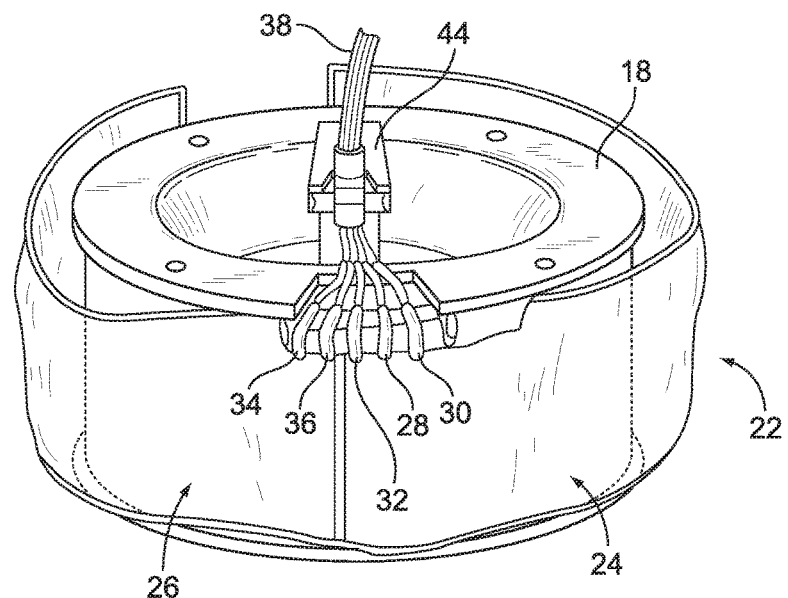
FIG. 3 is a top perspective view of the spool of the centrifuge shown in FIG. 2 in its upright position and carrying the blood separation chamber.

As FIGS. 3 and 4 best show, there are three ports 28, 30, and 32 associated with the first stage 24. Depending on the particular blood processing procedure, the ports may have different functionality but, in an exemplary procedure, the port identified at 32 may be used for conveying blood (which may include anticoagulant) from a blood source or donor into the first stage 24. During such a procedure, the other two ports 28 and 30 may serve as outlet ports for separated blood components exiting the first stage 24. For example, the first outlet port 30 may convey a low density blood component from the first stage 24, while the second outlet port 28 may convey a high density blood component from the first stage 24.

In a method of carrying out single-stage processing, one of the separated components is returned to the donor, while the other is removed from the first stage 24 and stored. For example, when carrying out a therapeutic plasma exchange procedure, whole blood in the first stage 24 is separated into cellular components (i.e., a high density red blood cell component) and substantially cell-free plasma (i.e., a low density component). The plasma is removed from the first stage 24 via the first outlet port 30 for collection and storage, while the cellular components are removed from the first stage 24 via the second outlet port 28 and returned to the donor or patient. Alternatively, rather than collecting and storing the plasma, it may instead be discarded after separation or treated by a secondary device and returned to the donor or patient.

If multi-stage processing is required, for example in a platelet collection procedure, one of the components (platelet-rich plasma) will be transferred from the first stage 24 to the second stage 26 via a port 34 associated with the second stage 26. The component transferred to the second stage 26 is further fractionated into sub-components such as plasma and platelet concentrate, with one of the sub-components (plasma in one embodiment) being removed from the second stage 26 via an outlet port 36 and the other sub-component (platelet concentrate in one embodiment) remaining in the second stage 26. In the illustrated embodiment, the ports 28, 30, 32, 34, and 36 are arranged side-by-side along the top transverse edge of the chamber 22.

While the same ports 28, 30, and 32 of the first stage 24 are used as in the above-described therapeutic plasma exchange procedure, the ports 28 and 32 may have different functionality in a multi-stage separation procedure. In the method of multi-stage operation for platelet collection, blood enters the first stage 24 via the port 28 and is separated into red blood cells (i.e., the high density blood component) and platelet-rich plasma (i.e., the low density blood component). The red blood cells are returned to the donor (via the port 32), while the platelet-rich plasma is conveyed out of the first stage 24 (via the first outlet port 30) and into the second stage 26 (via the inlet port 34). In the second stage 26, the platelet-rich plasma is separated into platelet-poor plasma and platelet concentrate. The platelet-poor plasma is removed from the second stage 26 (via the outlet port 36), leaving platelet concentrate in the second stage 26 for eventual resuspension and transfer to one or more storage containers.

As best shown in FIG. 3, a tubing umbilicus 38 is attached to the ports 28, 30, 32, 34, and 36. The umbilicus 38 interconnects the rotating first and second stages 24 and 26 with each other and with pumps and other stationary components located outside the rotating components of the centrifuge assembly 14 (see FIGS. 1 and 2). As FIG. 1 shows, a non-rotating (zero omega) holder 40 holds the upper portion of the umbilicus 38 in a non-rotating position above the spool 18 and bowl 16. A holder 42 on the yoke 20 rotates the mid-portion of the umbilicus 38 at a first (one omega) speed about the suspended spool 18 and bowl 16. Another holder 44 (FIGS. 2 and 3) mounts the lower end of the umbilicus 38 to the centrifuge assembly 14. The inherent strength of the umbilicus 38 causes the centrifuge assembly 14 to rotate at a second speed twice the one omega speed (the two omega speed). This known relative rotation of the umbilicus 38 keeps it from accumulating twisting, in this way avoiding the need for rotating seals. In an alternative embodiment, rather than the holder 42 rotating the umbilicus 38 to turn the centrifuge assembly 14, a gear system may be employed to rotate the umbilicus 38 and/or the centrifuge assembly 14 separately. It should be noted that the present subject matter can also be employed in direct-drive centrifuge assemblies (i.e., systems that rely on a gear train to rotate the centrifuge) and centrifuge assemblies using rotating seals, and is not limited to use in a seal-less centrifuge system.

As FIG. 4 shows, a first interior seal 46 is located between the low density outlet port 30 and the high density outlet port 28. A second interior seal 48 is located between the high density outlet port 28 and the blood inlet port 32. The interior seals 46 and 48 form a fluid passage 50 (an inlet for whole blood in an exemplary platelet collection procedure or an outlet for high density blood components in an exemplary therapeutic plasma exchange procedure) and a low density collection region 52 in the first stage 24. The second seal 48 also forms a fluid passage 54 (an outlet for high density blood components in an exemplary platelet collection procedure or a blood inlet in an exemplary therapeutic plasma exchange procedure) in the first stage 24.

In a platelet collection procedure, the fluid passage 50 channels blood into the first stage 24, where it separates into an optically dense layer 56 (FIG. 5), which forms as larger and/or heavier blood particles move under the influence of centrifugal force toward the high-G (outer) wall 62. The optically dense layer 56 will include red blood cells (and, hence, may be referred to herein as the "RBC layer") but, depending on the speed at which the assembly 14 is rotated, other cellular components (e.g., larger white blood cells) may also be present in the RBC layer 56.

Rather than flowing blood into the first stage 24 by the fluid passage 50 (as in a platelet collection procedure), blood enters the first stage 24 by the fluid passage 54 in a therapeutic plasma exchange procedure, but is still separated into an RBC layer 56. In comparison to a platelet collection procedure, the centrifuge assembly 14 rotates at a higher speed during a therapeutic plasma exchange procedure, creating a stronger separation field in the first stage 24. As a result of the stronger separation field, additional cellular components, namely white blood cells and platelets, will be present in a greater quantity in the RBC layer 56.

In both cases, the movement of the component(s) of the RBC layer 56 displaces less dense blood components radially toward the low-G (inner) wall 64, forming a second, less optically dense layer 58. In an exemplary platelet collection procedure, the less optically dense layer 58 includes platelet-rich plasma (and, hence, will be referred to herein as the "plasma layer"). In an exemplary therapeutic plasma exchange procedure, the less optically dense layer 58 includes substantially cell-free plasma. However, depending on the speed at which the centrifuge assembly 14 is rotated and the length of time that the blood is resident in the centrifuge assembly, other components (e.g., smaller white blood cells) may also be present in the plasma layer 58.

Figure 5:
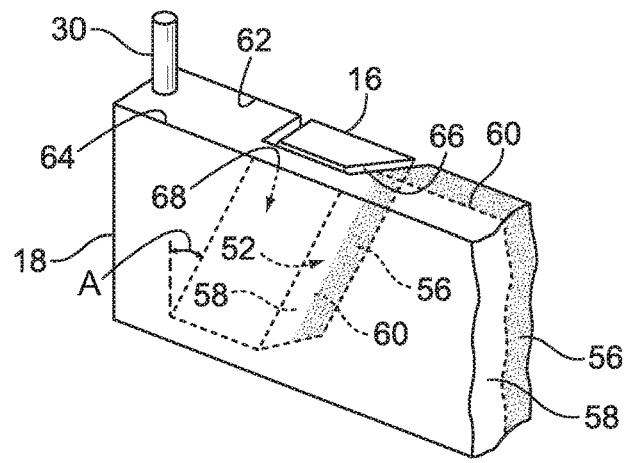
FIG. 5 is an enlarged perspective view of an interface ramp carried by the centrifuge in association with the blood separation chamber, showing the centrifugally separated red blood cell layer, plasma layer, and interface within the chamber when in a desired location on the ramp.

The transition between the RBC layer 56 and the plasma layer 56 is generally referred to as the interface 60 (FIG. 5). Platelets and white blood cells (which have a density greater than plasma and usually less than red blood cells) typically occupy this transition region, although that also varies with centrifuge speed and residence time, as is well known in the technical field.

Figure 6:
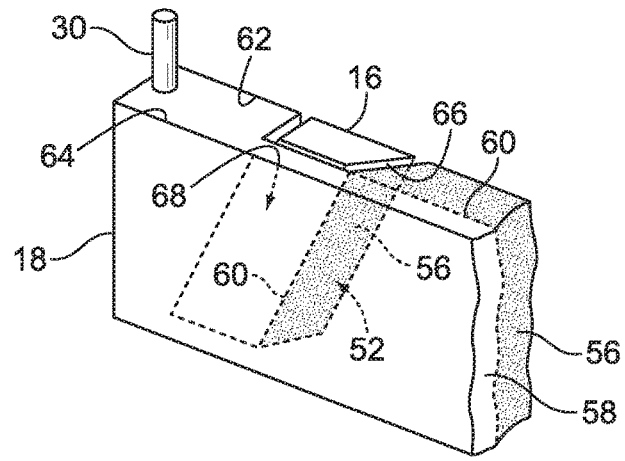
FIG. 6 is an enlarged perspective view of the interface ramp shown in FIG. 5, showing the red blood cell layer and interface at an undesired high location on the ramp.
Figure 7:
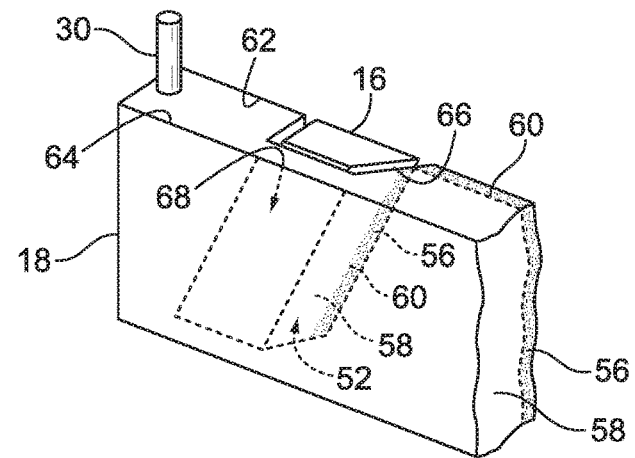
FIG. 7 is an enlarged perspective view of the interface ramp shown in FIG. 5, showing the red blood cell layer and interface at an undesired low location on the ramp.

The location of the interface 60 within the chamber 22 can dynamically shift during blood processing, as FIGS. 6 and 7 show. If the location of the interface 60 is too high (that is, if it is too close to the low-G wall 64 and the removal port 30, as FIG. 6 shows), cellular components can spill over and into the low density collection region 52, potentially adversely affecting the quality of the low density components (typically plasma). On the other hand, if the location of the interface 60 is too low (that is, if it resides too far away from the low-G wall 64, as FIG. 7 shows), the collection efficiency of the system 10 may be impaired.

In the illustrated embodiment, as FIG. 5 shows, a ramp 66 extends from the high-G wall 62 of the bowl 16 at an angle "A" across the low density collection region 52. The angle "A," measured with respect to the axis of the first outlet port 30 is about 25° in one embodiment. FIG. 5 shows the orientation of the ramp 66 when viewed from the low-G wall 64 of the spool 18. FIG. 4 shows, in phantom lines, the orientation of the ramp 66 when viewed from the high-G wall 62 of the bowl 16.

Further details of the angled relationship of the ramp 66 and the first outlet port 30 can be found in U.S. Pat. No. 5,632,893 to Brown et al., which is incorporated herein by reference. The ramp 66 shown in FIGS. 5-7 may be considered a simplified or representational version of an actual ramp that would be used in practice. For example, FIGS. 8-9 and 13-14 illustrate a particular ramp configuration that may be particularly advantageous for imaging and interface-detection purposes, as will be described in greater detail below. However, the ramp 66 may be variously configured without departing from the scope of the present disclosure.

The ramp 66 forms a tapered wedge that restricts the flow of fluid toward the first outlet port 30. The top edge of the ramp 66 extends to form a constricted passage 68 along the low-G wall 64. The plasma layer 58 must flow through the constricted passage 68 to reach the first outlet port 30.

As FIG. 5 shows, the ramp 66 makes the interface 60 between the RBC layer 56 and the plasma layer 58 more discernible for detection, displaying the RBC layer 56, plasma layer 58, and interface 60 for viewing through a light-transmissive portion of the high-G wall 62 of the chamber 22, as will be described in greater detail below.

Further details of the separation chamber 22 and its operation may be found in U.S. Pat. No. 5,316,667, which is incorporated by reference.

C. The Interface Controller

In one embodiment, the interface controller 12 (FIG. 16) includes an optical sensor system or assembly 70 (see FIGS. 8-12) positioned at a location outside of the centrifuge assembly 14. The optical sensor system 70 is oriented to detect the location of the interface 60 the RBC layer 56 and the plasma layer 58 on the ramp 66. If the interface 60 detected by the optical sensor system 70 is at an improper location (e.g., in the locations of FIG. 6 or 7), the interface controller 12 is functional to correct the location of the interface 60, as will be described in greater detail herein.

Referring to FIGS. 8-12, the optical sensor system 70 is secured to a fixture or wall 74 of the system 10. The wall 74 includes an opening 76 (FIG. 9) through which light from the optical sensor system 70 may be directed toward and into the centrifuge assembly 14 via a light-transmissive portion thereof. In the illustrated embodiment, the ramp 66 is translucent and comprises the light-transmissive portion of the centrifuge bowl 16, such that light from the optical sensor system 70 passes through the ramp 66 (FIGS. 13 and 14) to intersect the separated blood components thereon to determine the location of the interface 60, as will be described in greater detail herein.

The optical sensor system 70 includes a variety of components, some of which are contained within a housing or case 78. Among the components mounted within the housing 78 is at least one light source 80 (FIGS. 10-12), which emits a source beam 82 of light. The optical sensor system 70 may include one or more components (e.g., the achromatic prism pairs 84 and aperture stop 86 of FIGS. 10-12) configured to condition and/or focus the source beam 82 that exits the light source 80. For example, if provided, an achromatic prism pair 84 provides a color correction function by directing two color wavelengths (e.g., blue and red) along a desired path or angle, while an aperture stop 86 controls and limits the amount of light from the light source 80 allowed to pass further through the optical sensor system 70. It should be understood that, depending on the nature of the light source 80, selected components (e.g., the achromatic prism pairs 84) may be omitted from the optical sensor system 70. Similarly, additional components may also be incorporated into the optical sensor system 70 without departing from the scope of the present disclosure.

In the illustrated embodiment, the light source 80 comprises a light-emitting diode which emits a source light beam 82 or a plurality of light-emitting diodes that combine to emit a source light beam 82. The light source 80 may emit a single- or multiple-wavelength source light beam 82, but in a preferred embodiment, comprises a white light source that is configured to emit a multi-wavelength, white source light beam 82. If provided as a white light source, the light source 80 may comprise one or more true white lights (e.g., incandescent or filament lights or light-emitting diodes) or a plurality of differently colored light sources (e.g., red, green, and blue light-emitting diodes arranged on a common die) that combine to simulate or approximate a white light. In one embodiment, the light source 80 is of the type which emits a white source light beam 82 exhibiting a relatively high spectral power distribution in the red and blue wavelength spectra, such as a warm white LUXEON® light-emitting diode of Philips Lumileds Lighting Company of San Jose, Calif.

In other embodiments, other types of light sources and source beams may be employed without departing from the scope of the present disclosure. For example, in another embodiment, the light source comprises one or more non-white, narrow spectrum light sources. The nature of the narrow spectrum light sources (e.g., whether they are provided as light-emitting diode or in some other form) and the source light beam emitted by the narrow spectrum light sources (e.g., the color of the light, if it is within the visible spectrum) may vary and is not limited to a particular type of light source or a particular wavelength of light. In one exemplary embodiment, a narrow spectrum light source comprises a light-emitting diode configured to emit a red source light beam, in which case the light source may be provided as a deep red LUXEON® light-emitting diode of Philips Lumileds Lighting Company of San Jose, Calif. Other narrow spectrum red light sources may also be employed, as well as other narrow spectrum light sources configured to emit a beam having any other suitable wavelength. If the light source is configured to emit a relatively wide bandwidth source beam, it may be preferred to also provide one or more filters configured to narrow the bandwidth of either the source beam emitted by the light source and/or the bandwidth of a light beam returning to the optical sensor system 70 after having interacted with the fluid processing region.

Figure 15:
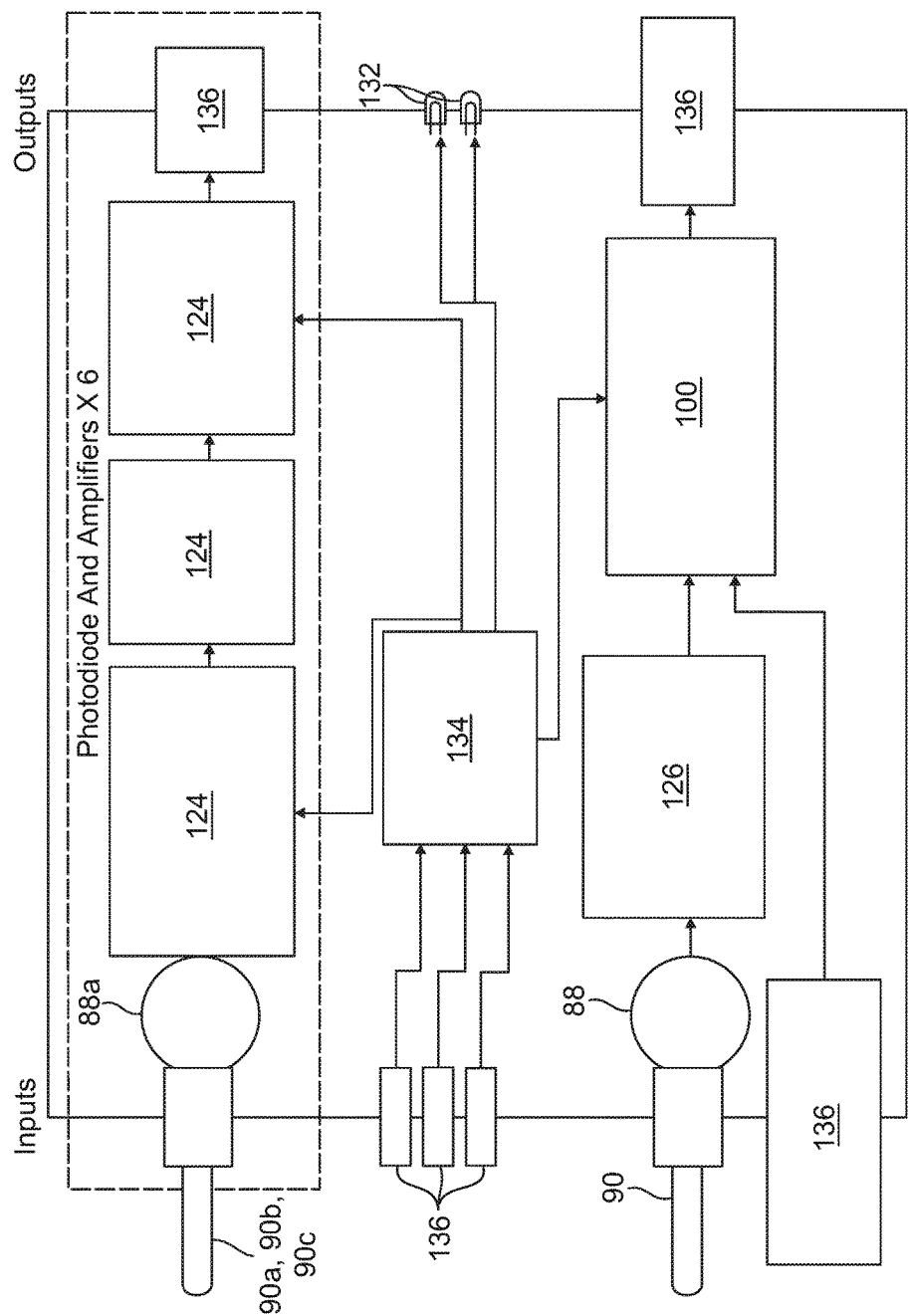
FIG. 15 is a schematic view of the interconnectivity of selected electronic components of the optical sensor system of FIG. 8.

The optical sensor system 70 also includes a plurality of light detectors 88, 88*a* (FIG. 15). The light detectors 88, 88*a* may be variously configured without departing from the scope of the present disclosure, but in one embodiment they comprise silicon PIN photodiodes, which may be particularly well-suited for use with a white or red light source. In the illustrated embodiment, the light detectors 88, 88*a* are positioned outside of the housing 78, and may be mounted in a separate housing. This may be advantageous for the purpose of spacing the light detectors 88, 88*a* and other sensitive components (e.g., analog electronics and amplifier components) away from the drive systems that rotate the centrifuge assembly 14. Additionally, such a configuration allows for a compact optical module design, which is relatively immune to electrical noise and vibration while allowing for electrically immune light transmission from the optical module to a separate electronics module that can be modified and upgraded for different functionality without affecting the optical module design. For example, if not otherwise provided, a separate electronics module could be modified and upgraded to include spectral splitting and analysis without modifying the optical module.

In embodiments having the light detectors 88, 88*a* mounted outside of the housing 78, they may be in communication with the interior of the housing 78 via optical fibers 90-90*c* (FIGS. 8-10 and 15). In the illustrated embodiment, there are four optical fibers 90-90*c* (one referred to herein as a reference fiber 90 and the others referred to herein as scanning fibers 90*a*-90*c*) extending between the housing 78 and four light detectors 88, 88*a* connected thereto by FC/PC connectors or the like to define a portion of the light path between the light source and the light detectors (FIG. 15 is simplified to show only one detector 88*a*, but in the illustrated embodiment there are a plurality, preferably three or six, of such detectors 88*a*). However, in other embodiments, there may be a different number of optical fibers and light detectors, at least one and preferably a plurality, such as three or more. For example, a beam splitter may be positioned at a downstream end of an optical fiber to split a beam exiting the optical fiber into two beams, with each beam going to a different light detector.

Figure 10:
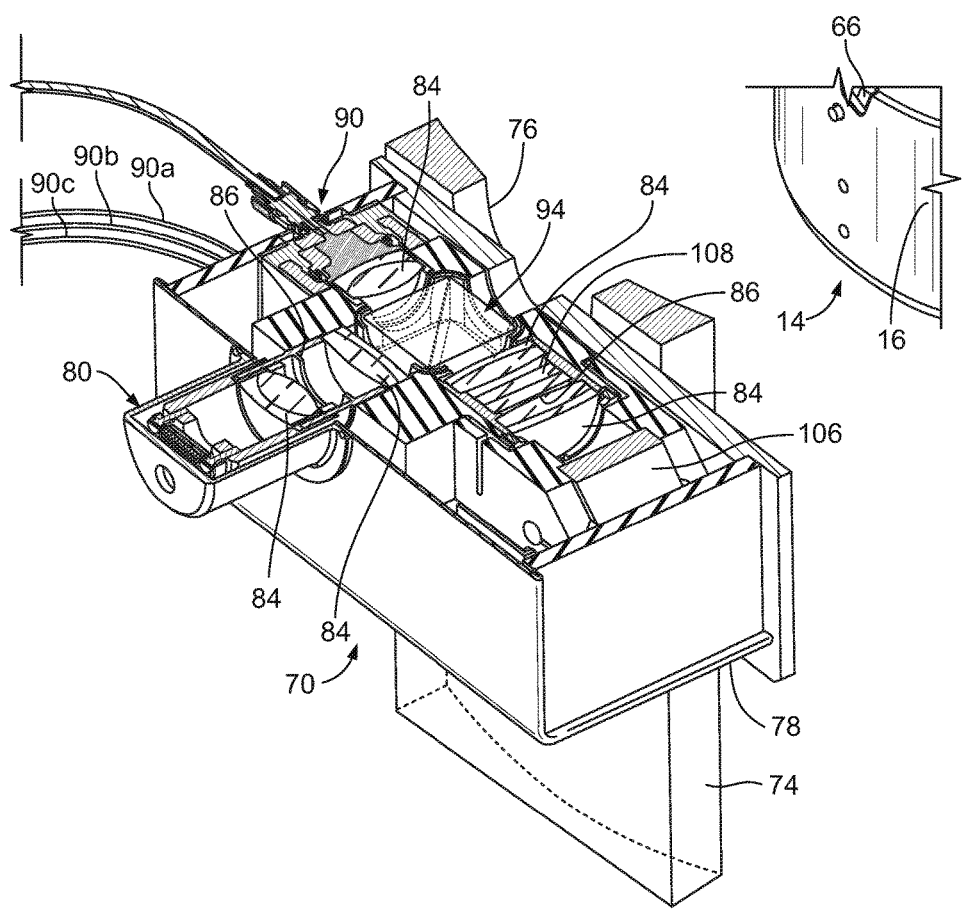
FIG. 10 is a cross-sectional view of the optical sensor system or assembly of FIG. 8.
Figure 11:
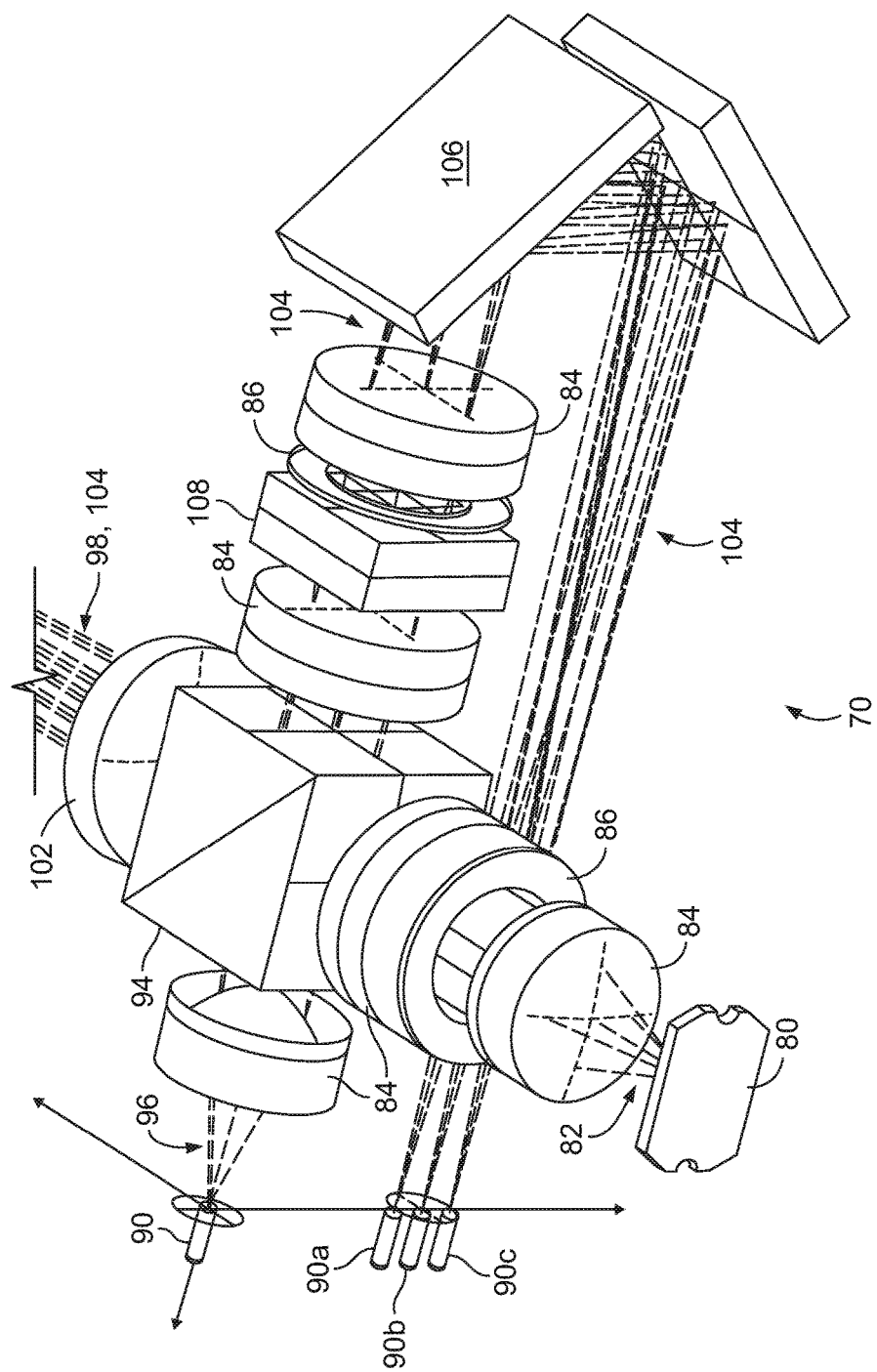
FIG. 11 is a perspective view of selected internal components of the optical sensor system or assembly of FIG. 8, with a housing or case of the optical sensor assembly omitted for illustrative purposes.

In the illustrated embodiment, the upstream or inlet (light-receiving) ends of the optical fibers 90-90*c* are oriented at an angle to the initial direction 92 of the source light beam 82, as shown in FIGS. 10-12. In one embodiment, the upstream or inlet ends of the optical fibers 90-90*c* are positioned to receive light along a direction perpendicular to the initial direction 92 of the source light beam 82. The optical fibers 90-90*c* are configured to receive at least a portion of the light emitted by the light source 80, so selected components of the optical sensor system 70 may be configured to direct light from the light source 80 toward one or more of the optical fibers 90-90*c*. For example, in the illustrated embodiment, the optical sensor system 70 includes a beam splitter 94 that is configured to split the source beam 82 from the light source 80 into two beams 96 (reference beam or first split beam) and 98 (scanning beam or second split beam) (FIGS. 11 and 12). In one embodiment, the beam splitter 94 comprises a beam splitter cube which splits the source beam 82, with a first split beam 96 being a reference beam that is reflected at an angle (e.g., 90° in the illustrated embodiment) toward the optical fiber 90 and a second split beam 98 being a scanning beam that is transmitted through the beam splitter cube 94 and toward the centrifuge assembly 14.

The optical sensor system 70 may include one or more components (e.g., an achromatic prism pair 84 for color correction, as shown in FIGS. 10-12) configured to condition and/or focus the reference beam 96 before it reaches the associated optical fiber 90, but the light received by the optical fiber 90 is essentially a direct view of the source beam 82 (albeit at a fraction of its original intensity) and gives an indication of the power level of the light source 80. For this reason, the optical fiber 90 that receives the reference beam 96 may be referred to as the reference fiber. As such, the reference fiber 90 may be associated with a light detector 88 that forms a feedback loop with a driver 100 of the light source 80 (FIG. 15). It may be advantageous for the light source 80 to emit a source beam 82 having a substantially uniform or constant brightness, and any fluctuations in the brightness of the source beam 82 are directly reflected in the brightness of the reference beam 96 and, hence, the strength of the signal transmitted from the light detector 88 to the driver 100. The driver 100 or a controller may make adjustments to the power delivered to the light source 80 to maintain the brightness of the source beam 82 at a substantially uniform level. In other embodiments, the brightness of the source beam 82 may be measured and used as an input to measure fluid characteristics (e.g., lipemia or hemolysis), apart from or in addition to the brightness being controlled. It is also within the scope of the present disclosure for the brightness to be measured to determine light output degradation over time, either apart from or in addition to the brightness being controlled. The light detector 88 may be directly associated with the driver 100 or, as shown in FIG. 15, include one or more intermediate devices (e.g., an interface processing module 126) that may measure or condition or otherwise interact with the signal from the light detector 88 prior to reaching the driver 100 or otherwise use the signal for other purposes.

Figure 11A:
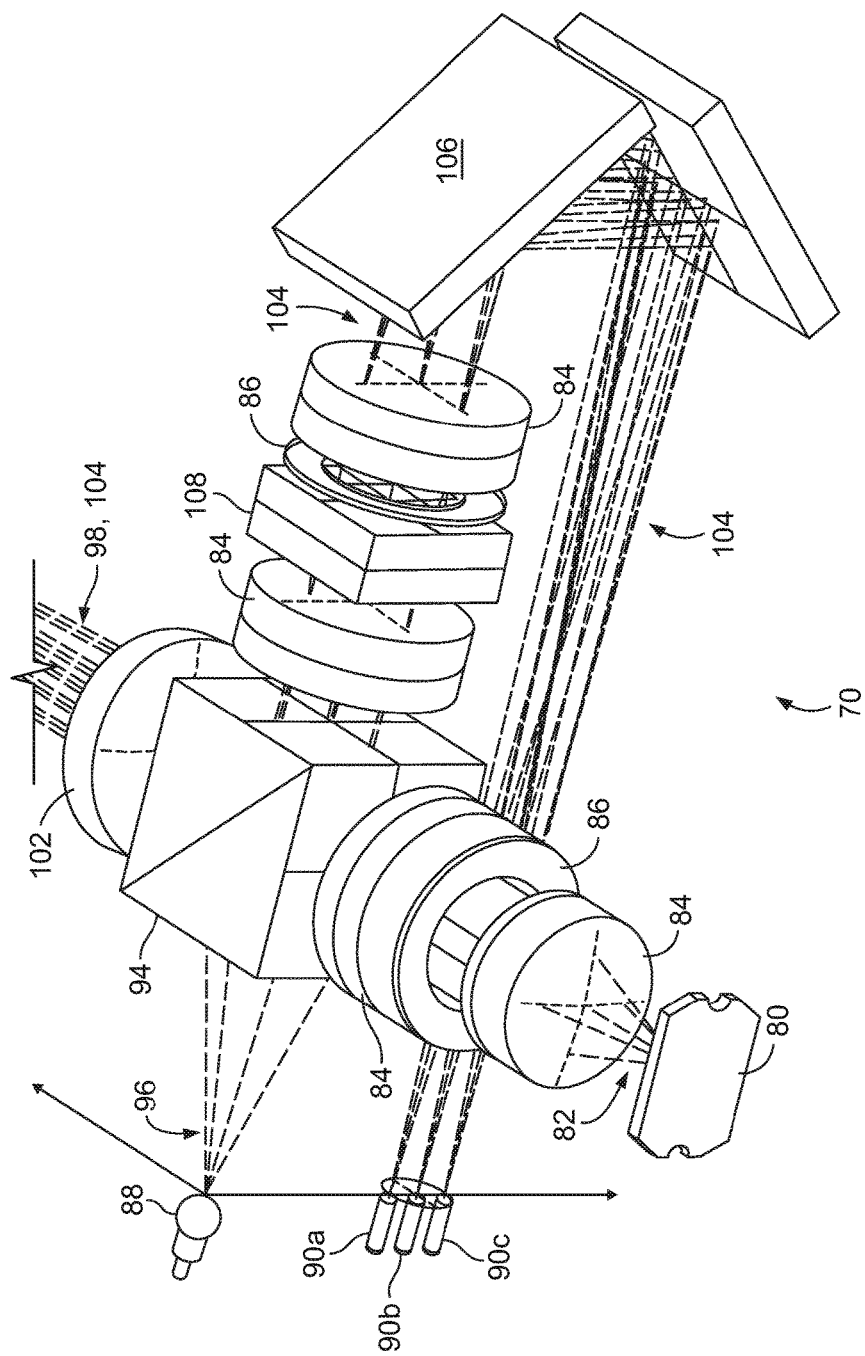
FIG. 11A is a perspective view of an alternative embodiment of the selected internal components of the optical sensor system of FIG. 11.

In an alternative embodiment, the reference fiber 90 is eliminated and the light detector 88 that is positioned downstream of the reference fiber 90 in the above-described embodiment is instead positioned within the housing 78. For example, FIG. 11A shows an embodiment in which the light detector 88 is placed in substantially the same location and in the same orientation as the reference fiber 90 in FIGS. 10 and 11. In such an embodiment, the light detector 88 directly receives light, rather than having light transmitted thereto by the reference fiber 90. By such a configuration, other components of the optical sensor system 70 (e.g., lens 84) may also be eliminated or modified. In other embodiments, one or more of the other optical fibers 90a-90c may be eliminated and replaced with a light detector that is positioned in the same or a similar position and orientation in the housing 78.

Figure 11B:
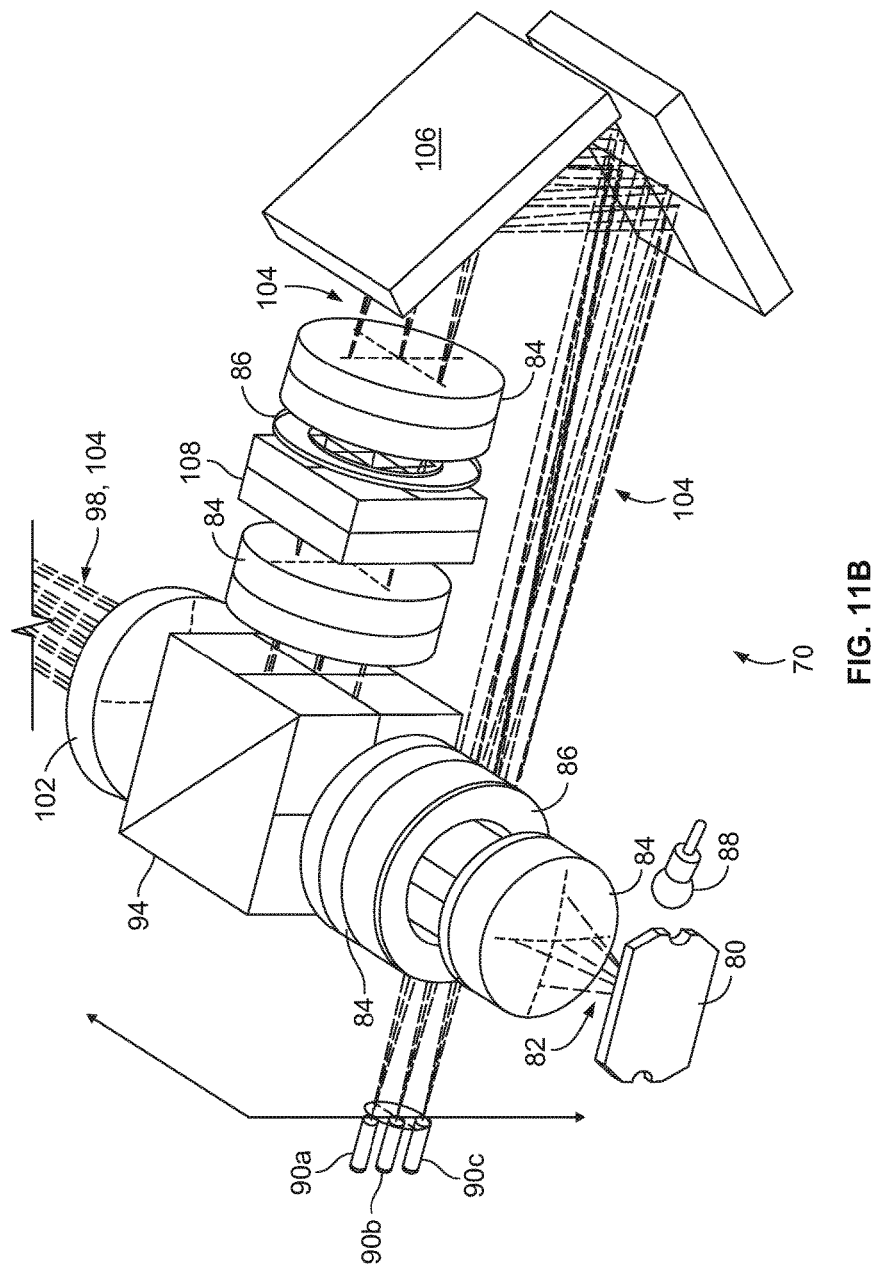
FIG. 11B is a perspective view of another alternative embodiment of the selected internal components of the optical sensor system of FIG. 11.

In another alternative embodiment which omits the reference fiber 90, the light detector 88 is placed in a different location within the housing 78 (FIG. 11B), rather than being positioned at the location of the reference fiber 90 in FIGS. 10 and 11. In the embodiment of FIG. 11B, the light detector 88 is positioned adjacent to the light source 80, which may include being positioned on the same printed circuit board as the light source 80 (if the light source 80 is mounted on a printed circuit board), but may include any other suitable location. By such a configuration, other components of the optical sensor system 70 (in addition to the reference fiber 90) may be eliminated or modified, as appropriate.

Depending on the exact location of the light detector 88, its orientation may vary, provided that it is oriented so as to be in at least partial light-receiving relationship with respect to the light source 80. In one embodiment, the light detector 88 is oriented at an angle with respect to the general path of the source beam 82. In the illustrated embodiment, a substantially side-looking light detector 88 is provided, with the light detector 88 being oriented generally perpendicular to the path of the source beam 82. In other embodiments, the light detector 88 may be positioned elsewhere within the housing 78 and oriented differently, but it has been found that a side-looking light detector 88 positioned adjacent to the light source 80 is particularly advantageous in terms of monitoring and controlling the level of light emitted by the light source 80.

Regardless of the exact location of the optical fibers and/or light detectors, the scanning beam 98 is transmitted through the beam splitter 94 (or other suitable light-directing member) and toward the centrifuge assembly 14. The scanning beam 98 may pass through a lens or protective window 102 prior to reaching the centrifuge assembly 14. The window 102 may serve a number of purposes, which may include focusing the scanning beam 98 at the proper location of the centrifuge assembly 14 and/or protecting the components of the optical sensor system 70 contained within the housing 78 from debris present within the system 10. As will be described in greater detail herein, the scanning beam 98 passes through the interface ramp 66 and the fluids positioned thereon (including the interface 60) before being reflected back to the optical sensor system 70. The reflected second split beam or reflected scanning beam 104 passes through the window 102 and encounters the beam splitter 94, which directs at least a portion of the reflected scanning beam 104 at an angle to the path 92 of the scanning beam 98 (FIG. 12). The path 92 of the scanning beam 98 coincides with the direction in which the reflected scanning beam 104 returns to the optical sensor system 70 (as well as the initial direction of the source light beam 82). In the illustrated embodiment, the beam splitter 94 directs at least a portion of the reflected second scanning 104 at a 90° angle to the path 92 of the scanning beam 98. Hence, it will be seen that the reflected scanning beam 104 is directed in the opposite direction of the reference beam 96 by the beam splitter 94.

In one embodiment, one or more optical fibers 90a-90c may be positioned to directly receive the reflected scanning beam 104 from the beam splitter 94 (i.e., being positioned along or adjacent to the same axis as the reference fiber 90, but oriented on the opposite side of the beam splitter 94 and facing the opposite direction). In another embodiment, such as the one illustrated in FIGS. 8-11, the optical fiber(s) 90a-90c configured to receive the reflected scanning beam 104 (which may be referred to as scanning fibers) are positioned generally adjacent to the reference fiber 90. More particularly, the illustrated scanning fibers 90a-90c are positioned below and in the same plane as the reference fiber 90, on the same side of the beam splitter 94 and facing in the same direction. Such a configuration may be advantageous for a number of reasons, such as space considerations and accessibility of the fibers for maintenance, replacement, and/or upgrade purposes. An optical barrier or other shielding surface may be interposed between the reference fiber 90 and the scanning fibers 90a-90c to prevent the reference beam 96 from illuminating the scanning fibers 90a-90c or the reflected scanning beam 104 illuminating the reference fiber 90.

In the illustrated embodiment, to facilitate the fiber positioning described above, a beam directing member 106 (e.g., a pair of mirrors) is employed between the beam splitter 94 and the scanning fibers 90a-90c to direct the reflected scanning beam 104 to the scanning fibers 90a-90c. The optical sensor system 70 may include one or more components (e.g., the achromatic prism pairs 84, direct vision prism 108, and aperture stop 86 of FIGS. 10-12) configured to condition and/or focus the reflected scanning beam 104 prior to encountering the beam directing member 106. A direct vision prism 108 may be particularly advantageous for undoing any dispersion of a reflected beam having passed through the ramp 66 (which may be prismatic, as described below), thereby color-correcting the reflected beam.

Figure 14:
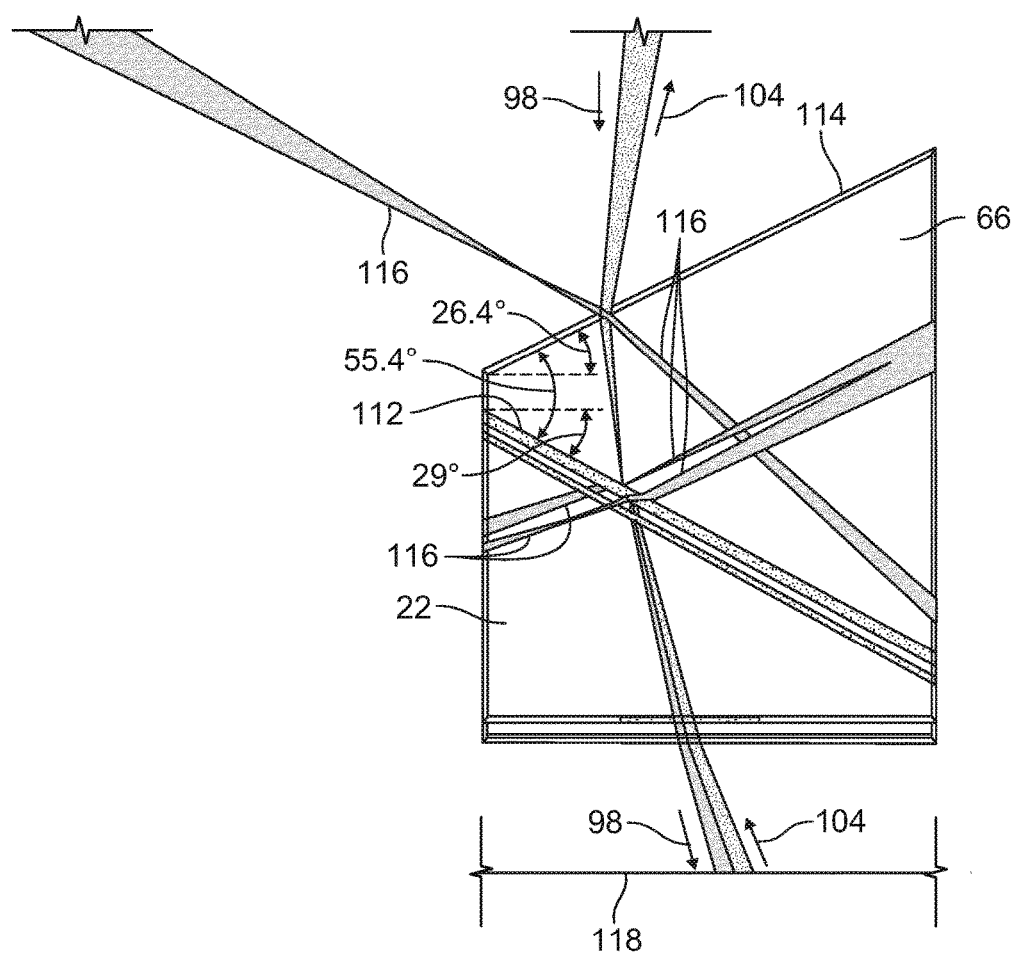

As for the relative position of the optical sensor system 70 with respect to the centrifuge assembly 14, FIG. 12 shows that the path 92 of the scanning beam 98 may be parallel to, but offset from, a radial line perpendicular to and passing through the rotational axis 110 of the centrifuge assembly 14. Hence, it can be seen that the beam emitted by the optical sensor system 70 to analyze the blood and/or blood components in the centrifuge assembly 14 neither passes through nor is parallel to the rotational axis 110 of the centrifuge assembly 14. This may be advantageous depending on the configuration of the ramp 66. For example, FIGS. 13 and 14 are cross-sectional views of the ramp 66, which shows it with an angled inner face 112 and an angled outer face 114, which effectively make the ramp 66 a prism. As used in reference to the faces of the ramp 66, the term "angled" refers to the fact that the inner and outer faces of the ramp 66 are non-tangential to the substantially circular perimeter of the bowl 16.

In the illustrated embodiment, the inner ramp face 112 is angled at approximately 29° (from a horizontal line, in the orientation of FIGS. 13 and 14) and the outer ramp face 114 is angled at approximately 26.4° (from a horizontal line, in the orientation of FIGS. 13 and 14), resulting in an approximately 55.4° prism. To minimize ghosting (show in FIG. 14 as rays 116) and maintain focus of light through the ramp 66 in view of the material (which may be a polycarbonate material in one embodiment) and configuration of the ramp 66 (i.e., as a prism), it has been found that causing the scanning beam 98 to encounter the outer ramp face 114 at an angle is advantageous. By offsetting the path 92 of the scanning beam 92 from the rotational axis 110 of the centrifuge assembly 14, the ramp 66 will be at an angle to the path 92 when the scanning beam 98 encounters the outer ramp face 114. In one embodiment, the ramp 66 is approximately 10° from center (see FIG. 12) when it comes into the field of vision of the optical sensor system 70. In other embodiments, it may be advantageous for the ramp 66 to be at a different angle or even centered when it comes into the field of vision of the optical sensor system 70.

As for the individual faces of the ramp 66, the inner ramp face 112 is angled to display the location of the interface 60, as described in greater detail above with respect to FIGS. 5-7. Accordingly, it is the inner ramp face 112 that the scanning beam 98 is focused upon to detect the location of the interface 60. The outer ramp face 114 is angled to contribute to focusing the scanning beam 98 on the inner ramp face 112 at all times that the ramp 66 is within the field of vision of the optical sensor system 70. Depending on the configuration of the optical sensor system 70, multiple samples or readings (of the order of one hundred, in some embodiments) can be taken each time the ramp 66 rotates through the field of view of the optical sensor system 70. FIGS. 13 and 14 illustrate two exemplary positions of the ramp 66 during a single pass of the ramp 66 through the field of vision of the optical sensor system 70, with FIG. 13 showing a portion of the right side of the inner ramp face 112 being scanned or viewed and FIG. 14 showing a portion of the left-center side of the inner ramp face 112 being scanned or viewed. It will be seen that, in both positions, the scanning beam 98 is focused on the inner ramp face 112, where the interface 60 is displayed.

Figure 8:
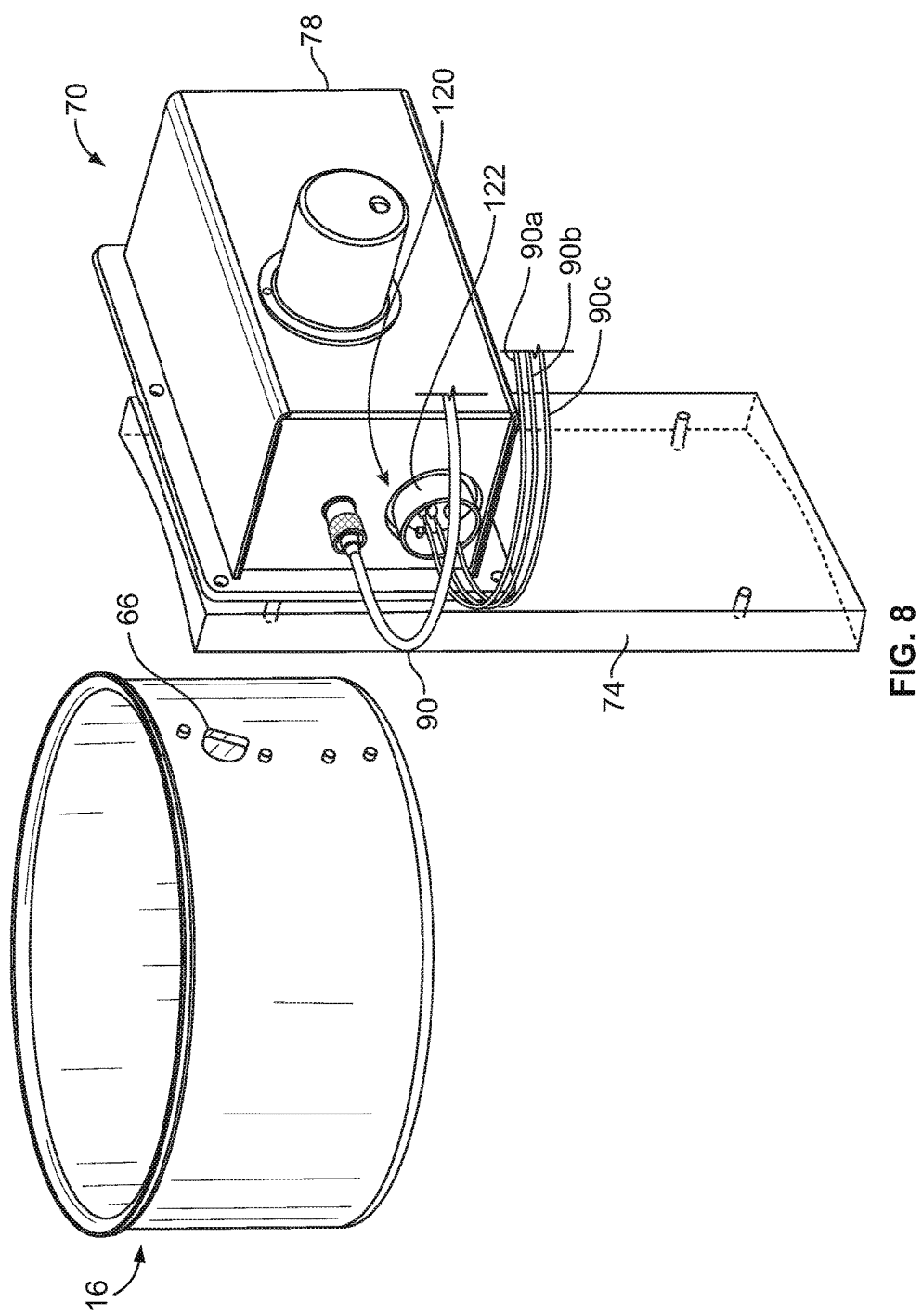
FIG. 8 is a front perspective view of the bowl of the centrifuge of FIG. 1 and an optical sensor system or assembly, inverted from the usual operating position for clarity, which may form a part of an interface controller to view the interface ramp during rotation of the bowl.
Figure 9:
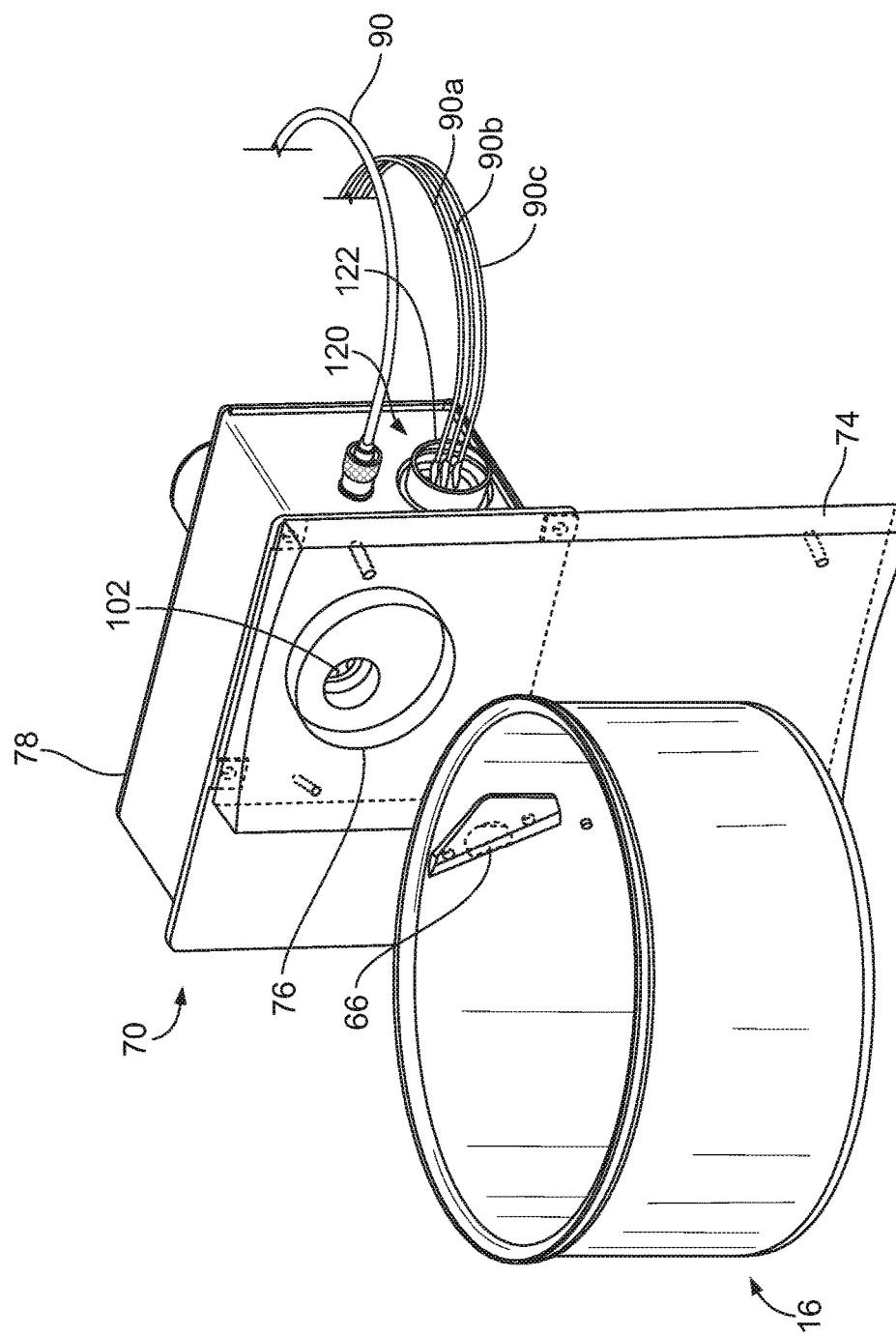
FIG. 9 is a rear perspective view of the bowl and optical sensor system or assembly of FIG. 8.

As shown in FIGS. 13 and 14 and noted above, at least a portion of the source beam 82 (which takes the form of the scanning beam 98 in the illustrated embodiment) is directed toward the rotating bowl 16 to pass through the light-transmissive portion thereof, the ramp 66, and the blood or blood component displayed thereon. In the illustrated embodiment, the bowl 16 is transparent to the light emitted by the light source 80 only in the region at which the interface ramp 66 is incorporated into the bowl 16 (FIGS. 8 and 12). In the illustrated embodiment, the region comprises a window or opening cut out in the bowl 16, which receives at least a portion of the ramp 66. The remainder of the bowl 16 that passes through the path of the optical sensor system 70 comprises an opaque or light absorbing material. In the illustrated embodiment, the optical sensor system 70 remains stationary during operation of the blood processing system 10, as the spool 18 and bowl 16 rotate at a two omega speed. Thus, the optical sensor system 70 may be provided as a continuous or an always-on system (i.e., shining light on the centrifuge assembly 14 even when the ramp 66 is out of the field of vision of the optical sensor system 70) or as an intermittent or gated system that only emits a source beam when the ramp 66 is within the field of vision.

The light from the source 80 passes through the ramp 66, to be focused on the inner ramp face 112 and the fluid displayed thereon (e.g., the separated blood components and interface 60). At least a portion of the light (i.e., the portion not absorbed or reflected by the fluids) continues through the blood separation chamber 22 and hits the spool 18. The spool 18 may carry a light-reflective material or light reflector 118 (FIGS. 13 and 14) behind the interface ramp 66 to return the light passing through the ramp 66, the fluid on the ramp 66, and the blood separation chamber 22. In the illustrated embodiment, the light reflector 118 comprises a retroreflector configured to reflect the light along the same path by which it strikes the retroreflector, as shown in FIGS. 13 and 14. It may be advantageous for the path 92 of the scanning beam 98 to coincide with the direction in which the reflected scanning beam 104 returns to the optical sensor system 70. For example, by employing coaxial scanning and reflected scanning beams 98 and 104, it is ensured that both beams 98 and 104 pass through the same optical components at substantially the same angles from the point where the source beam 82 enters the beam splitter 94 to the point where the reflected scanning beam 104 exits the beam splitter 94 to be focused on the scanning fibers 90a-90c. As used herein, the term "optical components" refers to the surfaces and objects through which a light beam passes. In the case of the scanning and reflected scanning beams 98 and 104, the optical components include the walls of the blood separation chamber 22, the fluids contained within the blood separation chamber 22, the ramp 66, the beam splitter 94, and the window 102. While it is preferred to employ a retroreflector to provide substantially coaxial scanning and reflected scanning beams 98 and 104, it is also within the scope of the present disclosure to employ a light reflector 118 comprising a mirror or the like, which reflects a light at the same angle at which the light is incident to the mirror. Light reflectors that reflect the scanning beam 98 at some other angle may also be employed without departing from the scope of the present disclosure.

The light reflected by the light reflector 118 passes again through the ramp 66, but in the other direction toward the optical sensor system 70 as a reflected beam or reflected scanning beam 104. The reflected beam 104 returned to the optical sensor system 70 is ultimately directed to one or more of the light detectors 88a for analysis. The reflected beam 104 may be directed to the light detector(s) in any suitable way without departing from the scope of the present disclosure, but in the illustrated embodiment, it is directed to a plurality of light detectors 88a via the operation of the beam splitter 94, the beam deflecting mirror 106, and the scanning fibers 90a-90c associated with the light detectors 88a, as described above in greater detail.

The reflected beam 104 is larger than the individual scanning fibers 90a-90c, so each scanning fiber will only receive a portion of the reflected beam 104. Accordingly, by arranging the scanning fibers in different configurations, different locations and portions of the reflected beam 104 may be captured and analyzed. For example, in the illustrated embodiment, three scanning fibers 90a-90c are arranged in a generally vertical line below the reference fiber 90 (FIG. 8), thereby taking readings of upper, lower, and central portions or locations of the reflected beam 104. While it is within the scope of the present disclosure for a single reference fiber or light detector to be used to analyze the reflected beam 104, it may be advantageous to employ a plurality of fibers and detectors to develop a more complete picture of the interface location. Additionally, the effect of noise on the signals ultimately received by the light detectors may be reduced by considering a plurality of readings from different locations, and accuracy improved.

As noted above, the ramp 66 may be oriented at an approximately 25° angle with respect to the rotational axis 110 of the centrifuge assembly 14, which results in the interface 60 appearing on the inner ramp face 112 as a line angled at an approximately 25° angle with respect to the rotational axis 110. If the scanning fibers 90a-90c are arranged in a vertical line (as shown in FIG. 8), they will register the presence of the interface 60 at different times. For example, in one embodiment, the upper end of the angled interface 60 may move into the field of vision of the optical sensor system 70 before the lower end does. In this case, at some point during a particular scanning session, the upper portion of the scanning beam 98 will pass through the interface 60 on the ramp 66 while the central and lower portions of the scanning beam 98 will pass through some other fluid on the ramp 66 (e.g., the RBC layer 56 or the plasma layer 58). At this point, the reflected beam 104 is returned to and received by the scanning fibers 90a-90c, with only the lowermost scanning fiber 90c being positioned to receive that portion of the reflected beam 104 that has passed through the interface 60 (on account of the illustrated beam directing member 106 inverting the image of the reflected beam 104). As the centrifuge assembly 14 continues to rotate through the field of vision of the optical sensor system 70, the lower portions of the scanning beam 98 will eventually pass through the interface 60, to be registered by the central and uppermost scanning fibers at later points in time. Accordingly, the "interface" signals transmitted to the light detectors 88a associated with the scanning fibers 90a-90c will occur at different times to reflect the fact that the interface 60 appears as an angled line on the ramp 66.

In an alternative embodiment, rather than positioning the scanning fibers 90a-90c in a vertical line, they may be oriented at an angle, such as at an approximately 25° to coincide with the angle at which the ramp 66 is oriented with respect to the rotational axis 110 of the centrifuge assembly 14. As described above, the interface 60 appears on the ramp 66 as a line oriented at approximately the same angle as that of the ramp 66 with respect to the rotational axis 110 of the centrifuge assembly 14. Thus, by orienting the scanning fibers 90a-90c along a line at the same approximate angle as the ramp 66, they will be also be oriented at approximately the same angle as the interface 60 on the ramp 66. With the scanning fibers 90a-90c arranged at the same angle as the interface 60, the "interface" signals transmitted to the light detectors 88a associated with the scanning fibers 90a-90c will occur substantially simultaneously.

By considering the previous two examples of optical fiber orientations, it will be seen that the location of the scanning fibers 90a-90c effectively determines the locations on the ramp 66 that are being monitored by the optical sensor system 70. Thus, while the two different scanning fiber arrangements will detect the same location of the interface 60 on the ramp 66, they consider different regions of the ramp 66 in doing so. In one embodiment, to give the optical sensor system 70 additional flexibility, the scanning fibers 90a-90c may be mounted together on an adjustable module. In the illustrated embodiment, the scanning fibers 90a-90c are mounted together on an adjustable module 120 having a tubular collar 122 (FIG. 8) extending outside of the housing 78, which may be grasped and rotated to simultaneously adjust the arrangement of all of the scanning fibers 90a-90c. In other embodiments, the scanning fibers may be arranged for individual, rather than simultaneous adjustment, such as by providing an adjustable module or a surface of the housing with a plurality of sockets into which the various scanning fibers may be selectively inserted or removed to create different (e.g., non-linear) one- or two-dimensional scanning profiles. The optical sensor system 70 may be configured to have a horizontal resolution (i.e., a resolution in the plane of the centrifuge assembly 14) of approximately 100 μm or better, resulting in an accurate determination of the location of the interface 60.

As for the light detectors 88, 88a and their contribution to determining and adjusting the location of the interface 60 on the ramp 66, FIG. 15 shows a plurality of representative light detectors 88, 88a. The lower detector 88 is associated with the reference fiber 90, as described above to form a feedback loop with the light source driver 100 to control the brightness of the light source 80. The upper light detector 88a of FIG. 15 is associated with one of the scanning fibers 90a-90c. FIG. 15 only shows one such detector 88a, but there may be one or more such detectors 88a for each scanning fiber 90a-90c provided in the optical sensor system 70. Each of these light detectors 88a receives the portion of the reflected beam 104 transmitted thereto by the associated scanning fiber 90a-90c. Each light detector 88a converts the light into a signal that may pass through one or more amplifiers 124 (e.g., a transimpedance amplifier, a gain amplifier, and/or a buffer amplifier), if provided. The individual signals represent a characteristic of the fluid (e.g., the location of its interface) or the nature of the fluid on the ramp 66 at the location monitored by the associated scanning fiber 90a-90c. For example, in one embodiment, as the ramp 66 comes into alignment with the optical sensor system 70, the detector(s) 88a will first sense light reflected through the plasma layer 58 on the ramp 66. Eventually, the RBC layer 56 adjacent the interface 60 on the ramp 66 will enter the optical path of the optical sensor system 70. The RBC layer 56 absorbs at least a portion of the light and thereby reduces the previously sensed intensity of the reflected light. The intensity of the reflected light transmitted to the detector(s) 88a is indicative of the amount of light that is not absorbed by the RBC layer 56 adjacent to the interface 60.

The signal(s) from the optical sensor system 70 are transmitted to an interface processing module 126 (FIG. 16), which can determine the location of the interface 60 on the ramp 66 relative to the constricted passage 68. A more detailed discussion of the algorithms by which an exemplary interface controller receives and processes signals to determine the location of the interface on the ramp may be found in U.S. Pat. No. 6,312,607 to Brown et al., which is incorporated herein by reference.

Figure 16:
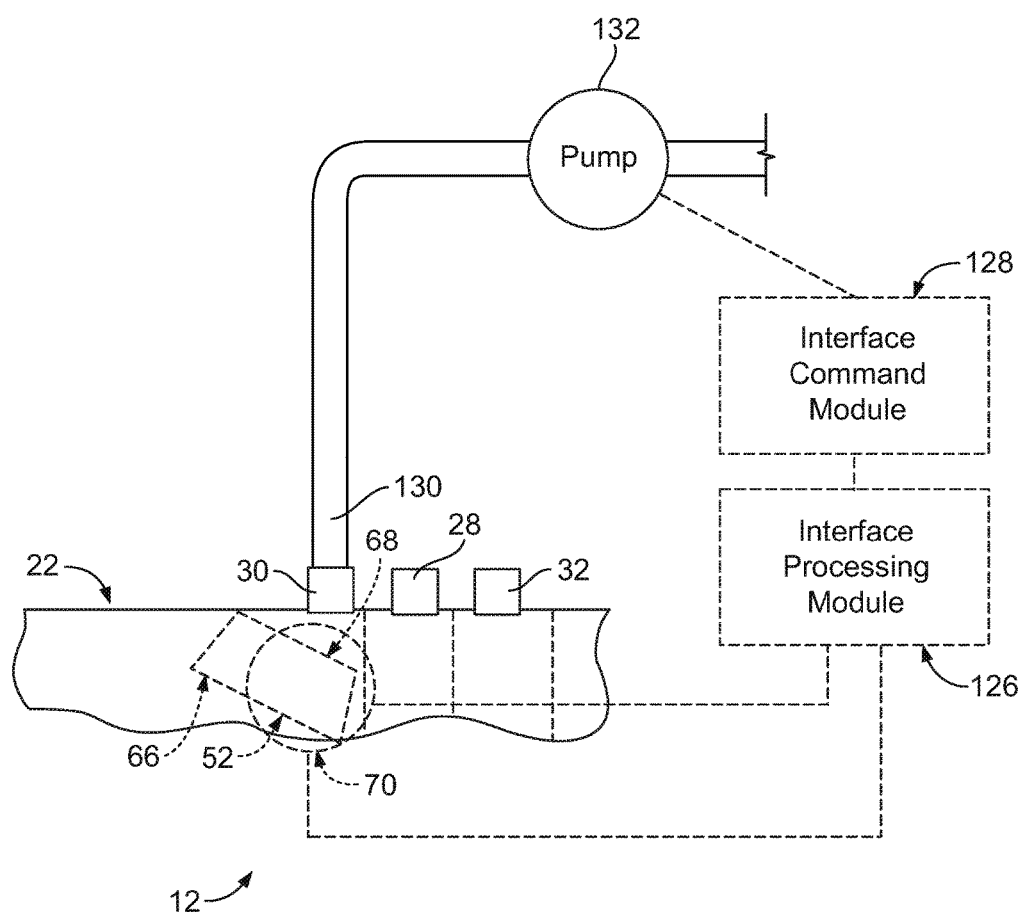
FIG. 16 is a schematic view of the interface controller, incorporating the optical sensor system of FIG. 8.

When the location of the interface 60 on the ramp 66 has been determined, the interface processing module 126 outputs that information to an interface command element or module 128 (FIG. 16). The interface command module 128 may include a comparator, which compares the interface location output with a desired interface location to generate an error signal. The error signal may take a number of forms but, in one embodiment, may be expressed in terms of a targeted red blood cell percentage value (i.e., the percentage of the ramp 66 which should be occupied by the RBC layer 56).

When the control value is expressed in terms of a targeted red blood cell percentage value, a positive error signal indicates that the RBC layer 56 on the ramp 66 is too large (as FIG. 6 shows). The interface command module 128 generates a signal to adjust an operational parameter accordingly, such as by reducing the rate at which plasma is removed through a tube 130 associated with the first outlet port 30 under action of a pump 132 (FIG. 16). The interface 60 moves away from the constricted passage 68 toward the desired control position (as FIG. 5 shows), where the error signal is zero.

A negative error signal indicates that the RBC layer 56 on the ramp 66 is too small (as FIG. 7 shows). The interface command module 128 generates a signal to adjust an operational parameter accordingly, such as by increasing the rate at which plasma is removed through the first outlet port 30 and associated tube 130. The interface 60 moves toward the constricted passage 68 to the desired control position (FIG. 5), where the error signal is again zero.

Besides determining the location of an interface, the optical sensor system 70 may determine other information about the fluid in the blood separation chamber 22. For example, the optical sensor system 70 may be configured to detect and read notations (e.g., bar codes) present on the centrifuge assembly 14 and/or the blood separation chamber 22. Alternatively, rather than intensity-based information, the optical sensor system 70 may be configured to gather spectrally-based information, thereby acting as a spectrometer. For example, when employing a white light source, different wavelengths of the light passing through the ramp 66 and fluid thereon will be absorbed by the different types of fluid that may appear on the ramp 66. The light that is reflected to a scanning fiber 90a-90c may be passed through a spectral beam splitter and then to a pair of light detectors 88a, with each detector receiving the unique wavelengths passed thereto and generating signals based on that data. The signals may be passed to a controller or processing module that considers the individual signals (e.g., considering red vs. blue light absorption) and/or compares them to historical signals (e.g., considering the difference in blue light absorption over time) to generate information about the fluid in the blood separation chamber 22 (e.g., lipid concentration, the presence of cellular blood components in separated plasma, platelet concentration, and hemolysis) and/or to cause adjustments in the operation of the system 10.

Furthermore, the optical sensor system 70 may include additional or alternative components without departing from the scope of the present disclosure. For example, FIG. 15 shows one or more power or status indicators 132 (which can be a visual indicator that the optical sensor system 70 is functional) and one or more voltage regulators 134 associated with the indicators 132, the driver 100, and various amplifiers 124. The system may also include various connectors 136 between the various components (e.g., BNC connectors, 3-pin connectors to a power source, etc.), as well as to other components that are not illustrated. In other embodiments, a non-white, non-LED light source and/or non-photodiode light detectors (e.g., a camera sensor or an area sensor array or a linear sensor array) may be employed and/or other illustrated components may be replaced with non-illustrated components suited to perform a similar or comparable function.

D. Alternative Centrifuge Yokes

As described above, centrifuge assemblies according to the present disclosure may be provided as umbilicus-driven (as illustrated in FIGS. 1 and 2) or as direct-driven. If the centrifuge assembly is umbilicus-driven, additional steps may be taken to reduce the risk of the view of the ramp 66 by the optical sensor system 70 being blocked or obscured by the yoke 20 or umbilicus 38 during use.

Figure 17:
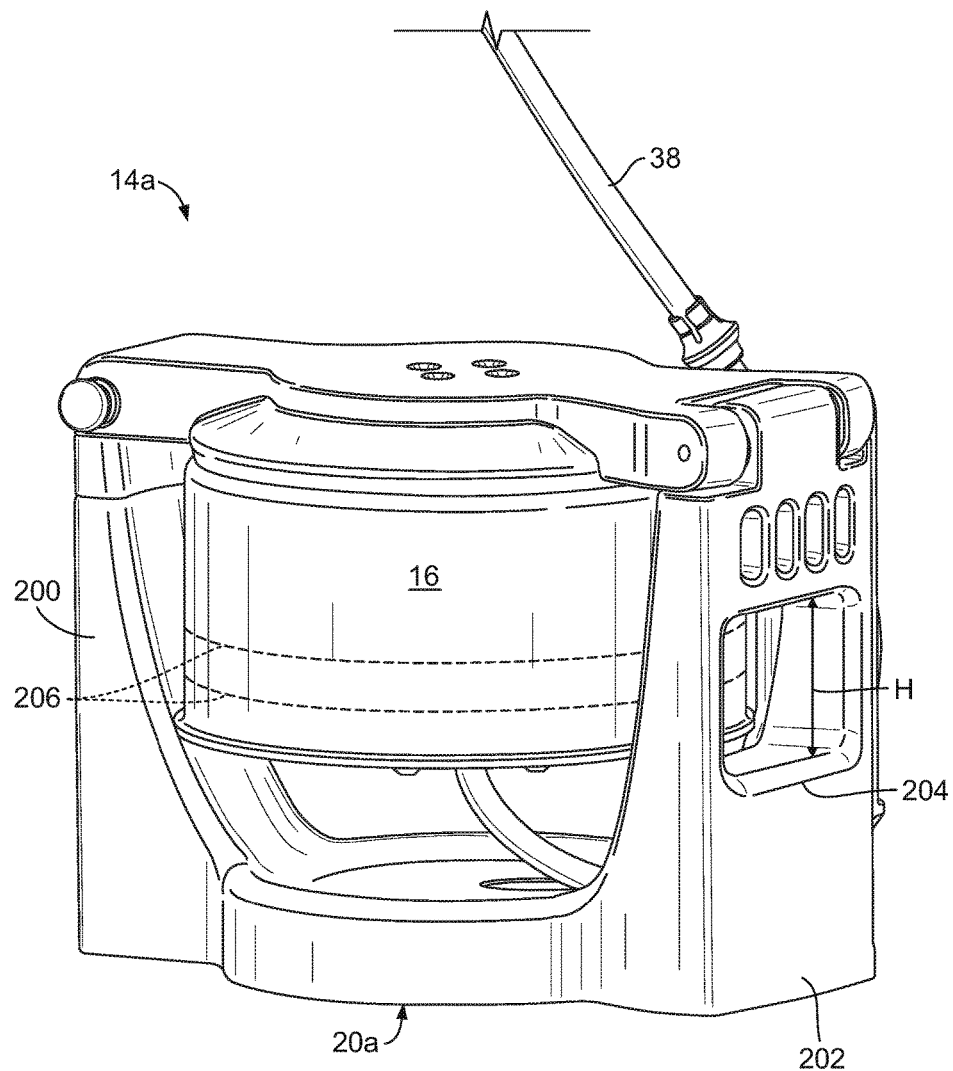
FIG. 17 is a perspective view of an alternative centrifuge yoke for use with optical sensor systems according to the present disclosure.
Figure 18:
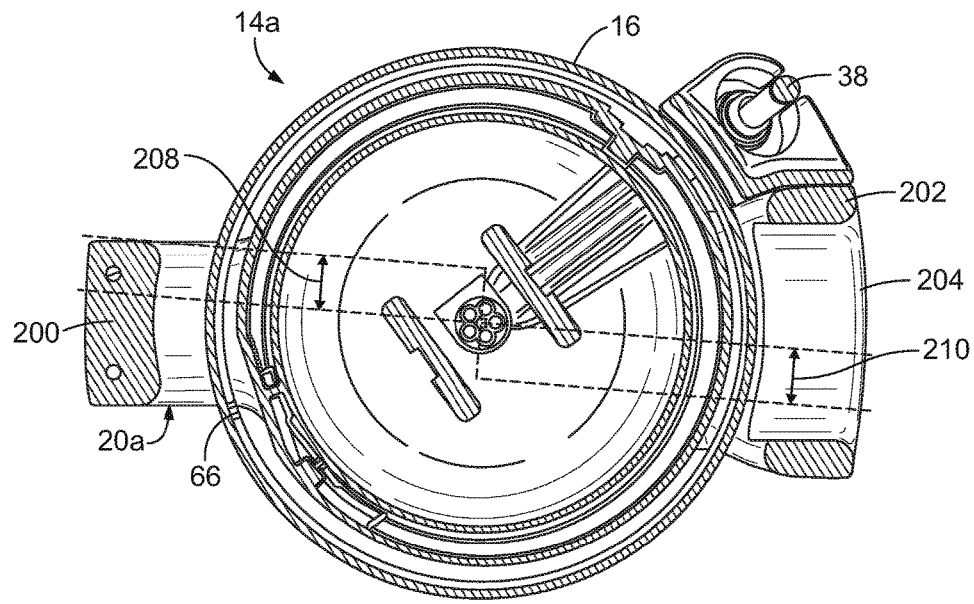
FIGS. 18 and 19 are cross-sectional views of the centrifuge and yoke of FIG. 17, showing sight lines into the centrifuge in different centrifuge positions.
Figure 19:
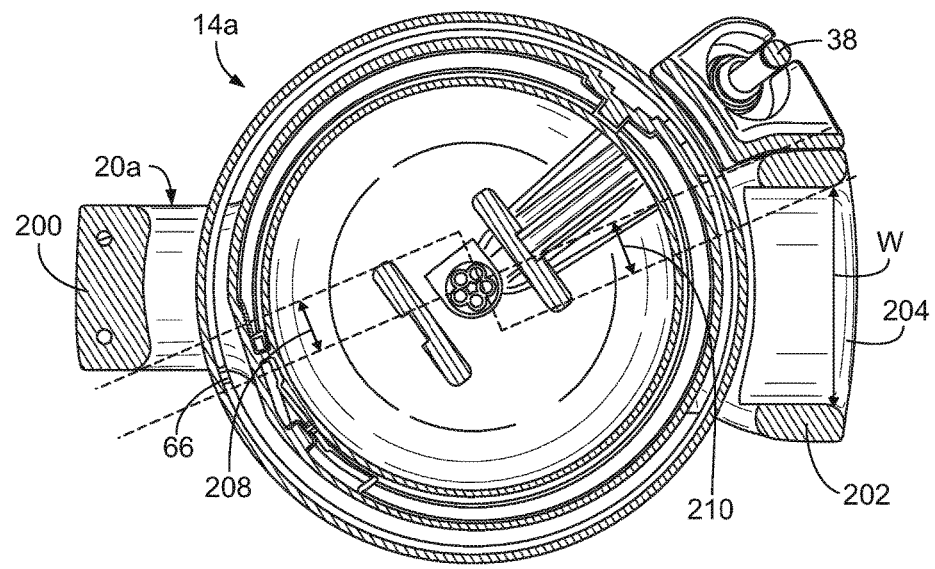

According to one approach, a centrifuge assembly 14a having a modified yoke 20a is provided, as shown in FIGS. 17-19. The yoke 20a includes first and second support arms 200 and 202, which are shown as being generally diametrically opposed, with the centrifuge bowl 16 positioned therebetween. The yoke 20a is configured and operates generally according to the above description of the yoke 20 of FIGS. 1 and 2, with the exception that one of the support arms (illustrated as second support arm 202) defines an opening or aperture or window 204 therethrough. As will be described in greater detail, the yoke window 204 is configured to provide a sight line through the support arm 202 to allow the optical sensor system 70 to view and monitor the ramp 66. Accordingly, the yoke window 204 is preferably significantly larger than the ramp 66 to maximize the visibility of the ramp 66 through the support arm 202, with a height H (the vertical dimension in the orientation of FIG. 17) that is greater than the height of the ramp 66 (shown in FIG. 17 as a pair of broken lines 206 to represent the multiple possible positions of the ramp 66 as the centrifuge bowl 16 is rotated) and a width or angular extent W (FIG. 19) that is greater than the width or angular extent of the ramp 66. Preferably, the yoke window 204 is positioned with the ramp 66 centered along the height H of the yoke window 204 (i.e., with the vertical center of the ramp 66 being at the same elevation as the vertical center of the yoke window 204 in the orientation of FIG. 17), but it is also within the scope of the present disclosure for the ramp 66 to be closer to the top or bottom of the yoke window 204.

Increasing the width or angular extent W of the yoke window 204 increases the visibility of the ramp 66 by the optical sensor system 70. As best shown in FIGS. 18 and 19, the yoke window 204 preferably has a width or angular extent W equal to or greater than that of the opposing support arm 200 at the same elevation, with the other support arm 200 being diametrically opposed to the yoke window 204. By such a configuration, there is never one visual obstruction or obstacle (e.g., one of the support arms 200, 202) positioned 180° from another visual obstruction or obstacle (e.g., the other support arm). By way of example, FIG. 18 shows opposing first and second sight lines 208 and 210 into the centrifuge bowl 16 from a position outside of the centrifuge assembly 14a (e.g., from the position of the optical sensor system 70). When the first sight line 208 is blocked by the first support arm 200 (FIG. 18), there is visibility into the centrifuge bowl 16 180° away along the second sight line 208 via the yoke window 204. When the second sight line 210 is blocked by the second support arm 202 (FIG. 19), there is visibility into the centrifuge bowl 16 180° away along the first sight line 200 to the side of the first support arm 200.

The illustrated configuration may be preferred because of the fact that the yoke 20a rotates at one half the speed of the centrifuge bowl 16, as described above in greater detail. In such a rotational relationship, a 180° rotation of the yoke 20a will result in a 360° rotation of the centrifuge bowl 16. Thus, the ramp 66 will be at the same position (e.g., in position to be viewed by the optical sensor system 70) upon each 180° rotation of the yoke 20a. Accordingly, if the yoke is provided with visual obstructions or obstacles positioned 180° apart, then it may be that the view of the ramp 66 will be obstructed during consecutive 360° rotations of the centrifuge bowl 16. In contrast, if the yoke is provided so as to eliminate any obstructions positioned 180° apart (as in the embodiment of FIGS. 17-19), then even if the view of the ramp 66 is obstructed at one time, the view of the ramp 66 by the optical sensor system 70 will be clear during the next 360° rotation of the centrifuge bowl 16.

In connection with the yoke 20a of FIGS. 17-19 (or provided separately), the optical sensor system 70 may include a component that can distinguish between an obstructed or partially obstructed view and an unobstructed view. This functionality may be incorporated one of the existing components (e.g., the interface processing module 126) or instead be provided by a separate component. In one embodiment, this is accomplished by bracketing the time it takes to scan the ramp 66 twice and comparing the pulse-widths of the two scans obtained during that time period. A partially obstructed scan will have a shorter pulse-width than an unobstructed scan, while a fully obstructed scan will have no pulse-width. By bracketing the time it takes to scan the ramp 66 twice, a fully obstructed scan with no pulse-width may be considered, whereas such a scan may be ignored or missed if the distinguishing device only detects and measures non-zero pulse-widths. When one of the scans has a greater pulse-width than the other, the scan having the larger pulse-width may be selected for further processing and use in the control system. If the pulse-widths of the scans are the same or approximately the same, either one or both of the scans may be selected for further processing and use in the control system. It should be understood that this bracketing method is only one way of distinguishing between obstructed and unobstructed views of the ramp 66, and other methods of distinguishing between obstructed and unobstructed views of the ramp 66 may be employed without departing from the scope of the present disclosure.

Figure 20:
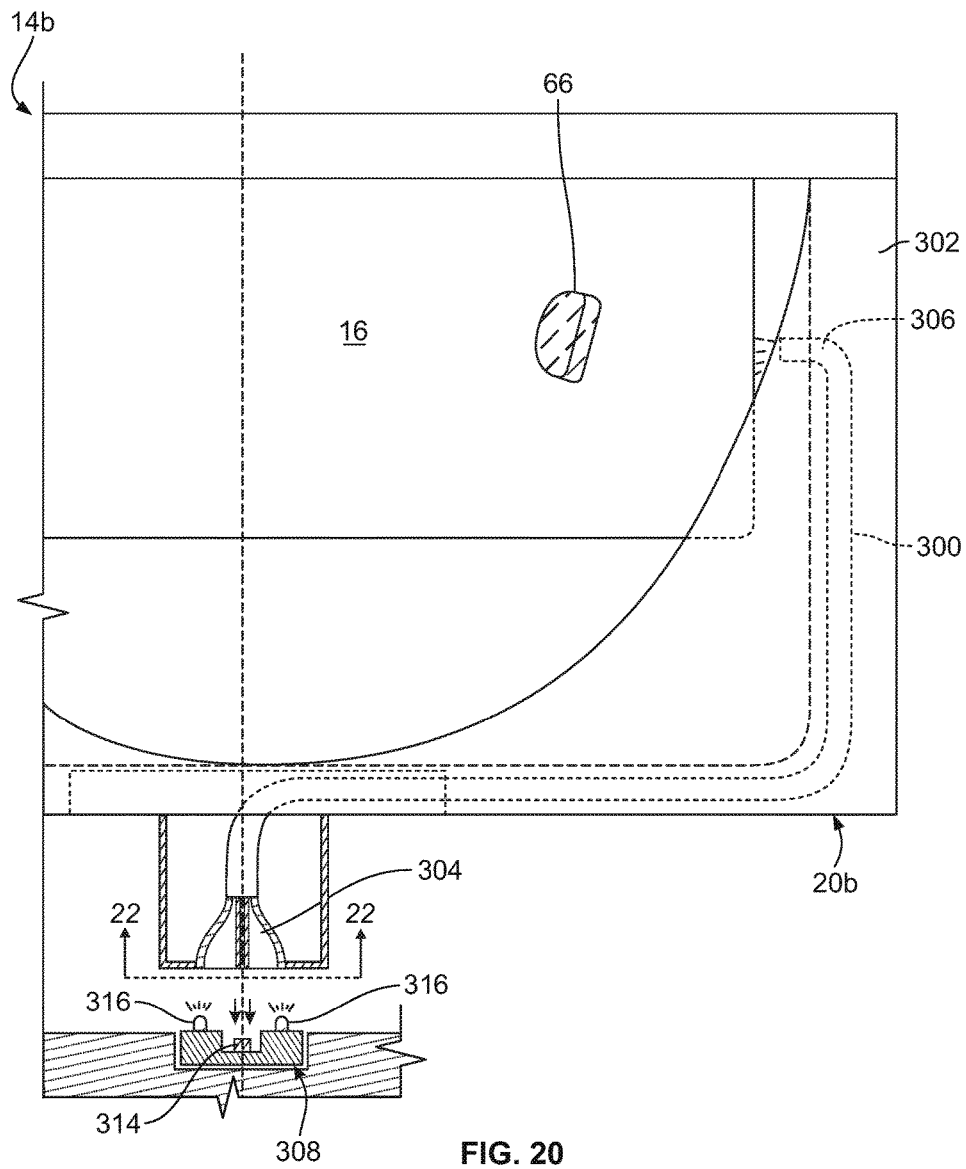
FIG. 20 is a partial cross-sectional view of another embodiment of an alternative centrifuge yoke for use with optical sensor systems according to the present disclosure.

While FIGS. 17-19 illustrate a two-armed yoke 20a, with one of the support arms 202 having a window 204 therethrough for improved visibility into the centrifuge bowl 16 from an externally located optical sensor system, it is also within the scope of the present disclosure to omit one of the support arms. For example, FIG. 20 shows only one support arm 302 of a yoke 20b. If the yoke 20b includes only one support arm 302, then the above-described concern of a visual obstruction located 180° away from the support arm 302 is effectively eliminated.

Figure 21:
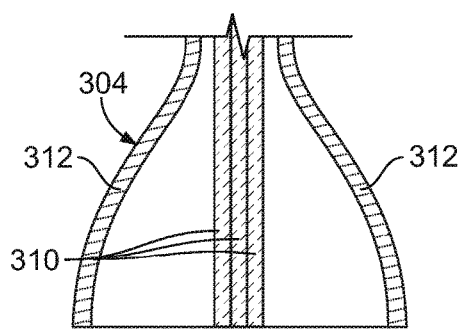
FIG. 21 is a cross-sectional detail view of a lower end of an optical fiber bundle associated with the yoke of FIG. 20.
Figure 23:
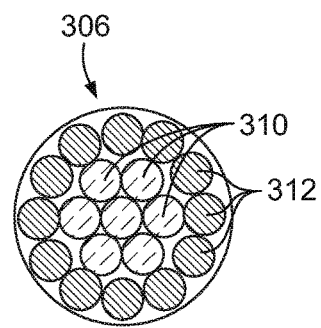
FIG. 23 is an end view of the upper end of the optical fiber bundle associated with the yoke of FIG. 20.
Figure 22:
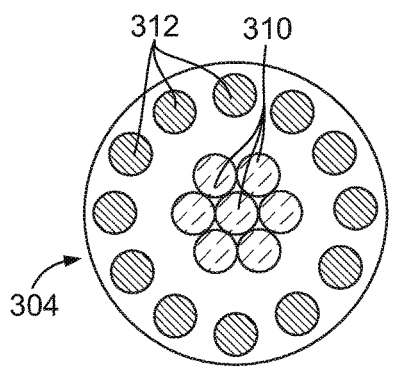
FIG. 22 is an end view of the lower end of the optical fiber bundle associated with the yoke of FIG. 20.

According to another aspect of the present disclosure that is illustrated in FIG. 20, a yoke 20b having an optical fiber bundle 300 associated therewith is provided. In the illustrated embodiment, an optical fiber bundle 300 is secured to an exterior and/or an interior portion one of the yoke support arms 302, but it is also within the scope of the present disclosure for a single optical fiber bundle to be associated with two yoke support arms or for separate optical fiber bundles to be associated with each yoke support arm (if more than one support arm is provided). The optical fiber bundle 300 extends between a first or lower end 304 and a second or upper end 306. The lower end 304 is illustrated in greater detail in FIGS. 21 and 22, while the upper end 306 is illustrated in greater detail in FIG. 23. The lower end 304 is oriented in light-receiving and light-transmitting relationship to an illumination and detection assembly or optical sensor system 308, which will be described in greater detail. The upper end 306 is directed toward the centrifuge bowl 16 of the centrifuge assembly 14b, in light-receiving and light-transmitting relationship to the ramp 66 of the centrifuge bowl 16. There may be an air gap between the upper and lower ends of the optical fiber bundle 300 and the centrifuge bowl 16 and illumination and detection assembly 308, respectively, thereby avoiding the need to use an optical slip ring or fiber optic rotary joint or the like.

Figure 23A:
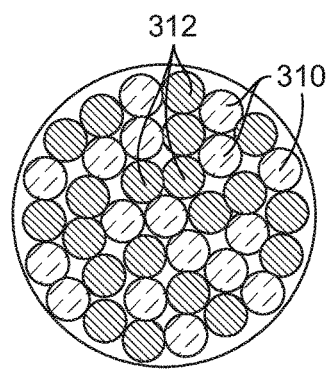
FIG. 23A is an end view of an alternative embodiment of the upper end of the optical fiber bundle associated with the yoke of FIG. 20.

The optical fiber bundle 300 includes one or more of signal fibers 310 and one or more illumination fibers 312, all of which are configured to transmit light between the ends 304 and 306 of the optical fiber bundle 300. In one embodiment, the signal fibers 310 are positioned at and directly adjacent to the central axis of the optical fiber bundle 300, while the illumination fibers 312 are positioned around the signal fibers 310, such as in a ring or annular arrangement. This configuration is advantageous when used in combination with the particular illumination and detection assembly 308 of FIG. 20, but other fiber configurations (such as the mixed arrangement of signal fibers 310 and illumination fibers 312 shown in FIG. 23A or a configuration that positions the illumination fibers 312 at and directly adjacent to the central axis of the optical fiber bundle 300, with the signal fibers 310 positioned around the illumination fibers 312) may be employed with differently configured illumination and light detection assemblies.

The illumination and detection assembly 308 of FIG. 20 includes at least one light detector 314 and at least one light source 316. The illustrated light detector(s) 314 and the light source(s) 316 are configured to correspond generally to the locations of the signal fibers 310 and illumination fibers 312, respectively. In particular, the illustrated illumination and detection assembly 308 comprises a central photodiode 314 or other suitable light detector aligned with the central axis of the optical fiber bundle 300 at its lower end 304 (to correspond to the location of the signal fibers 310 at and directly adjacent to the central axis of the optical fiber bundle 300) and a plurality of light-emitting diodes or laser diodes 316 or other suitable light sources arranged in a ring around the light detector 314 (to correspond to the location of the illumination fibers 312 at the lower end 304 of the optical fiber bundle 300). The light source(s) 316 may be spaced away from the light detector(s) 314 to prevent the light detector(s) 314 from receiving light from the light source(s) 316, in which case the lower end 304 of the optical fiber bundle 304 may be outwardly flared (FIGS. 21 and 22) to similarly separate the signal fibers 310 from the illumination fibers 310 and to maintain the fibers in proper registration with the associated components of the illumination and detection assembly 308.

In use, light is emitted by the light source(s) 316 in a direction substantially parallel to the rotational axis and received by the illumination fibers 310 at the lower end 304 of the optical fiber bundle 300. The illumination fibers 310 transmit the light to the upper end 306 of the optical fiber bundle 300, where it is directed onto the outer surface of the centrifuge bowl 16 in a generally radial direction, including the ramp 66 when it has rotated into light-receiving relationship with the upper end 306 of the optical fiber bundle 300. The light source(s) 316 may be configured to be always on or to only be on when the ramp 66 is in light-receiving relationship with the upper end 306 of the optical fiber bundle 300. Light from the illumination fibers 312 passes through the ramp 66 and the fluid thereon (as described above with respect to the embodiment of FIGS. 1-16). The light is reflected back through the ramp 66 and out of the centrifuge bowl 16 (by a retroreflector or mirror or the like, as described above with respect to the embodiment of FIGS. 1-16), where it is received by the signal fibers 310 at the upper end 306 of the optical fiber bundle 300. The signal fibers 310 transmit the reflected light from the upper end 306 of the optical fiber bundle 300 to the lower end 304 of the optical fiber bundle 300, where it is directed toward the light detector(s) 314. The light detector(s) 314 receives the light from the signal fibers 310 and transmits the data to a processor, such as the interface command module 126, for detecting and controlling the location of the interface on the ramp 66 and/or determining other information about the fluid on the ramp 66.

According to one embodiment, a wide variety of information may be determined about the fluid processing region by providing two or more light sources 316 configured to emit light having differing wavelengths. The light sources 316 may operate simultaneously or be controlled to function separately (e.g, by switching selected light sources 316 on during one sampling session or rotation of the centrifuge bowl 16 and the switching those light sources 316 off and other light sources 316 on during another sampling session or rotation of the centrifuge bowl 16) to direct light of differing wavelengths into the fluid processing region, which different wavelengths may be used to determine different information about the fluid processing region (e.g., lipemia or hemolysis or the location of the interface, etc.).

In the illustrated embodiment, the light detector(s) 314 and the light source(s) 316 are all positioned at the same general location, which may be at a non-rotating surface of the centrifuge assembly 14b along the axis of rotation, but it is also within the scope of the present disclosure for the components to be located at different locations. It is also within the scope of the present disclosure for the illumination and signal fibers to be positioned at different locations. For example, the illumination fibers 312 may be positioned as shown in FIG. 20, while the signal fibers 310 are at least partially positioned within the centrifuge bowl 16 to directly receive light from the illumination fibers 312 after it has passed through the ramp 66 (e.g., with the upper ends of the signal fibers 301 being located on the centrifuge spool behind the ramp 66, where the retroreflector or mirror would otherwise be to receive light transmitted through the ramp 66). The signal fibers 310 would then transmit the light from the illumination fibers 312 to the light detector 314, wherever it may be located.

Optical sensor systems of the type illustrated in FIG. 20 have several advantages. For example, such a design takes advantage of the proximity of the optical fiber to the fluid processing region to implement a non-imaging light collection system. This allows for more generous alignment and focusing tolerances and illumination requirements in comparison to other known optical sensor systems. Additionally, on account of the light being directed into the fluid processing region from a position that rotates in the same direction as the fluid processing region, the signal received from the fluid processing region may be longer than a signal resulting from light directed into the fluid processing region from a stationary position (e.g., on the order of twice the duration).

Systems of the type illustrated in FIG. 20 may be used alone or in combination with the other aspects described herein. For example, the system of FIG. 20 may be used in combination with the optical sensor system 70 to act as an auxiliary optical sensor system in the event that the view of the optical sensor system 70 becomes obscured or obstructed or to monitor a different aspect of the fluid on the ramp 66.

Aspects of the present subject matter described above may be beneficial alone or in combination with one or more other aspects. Without limiting the foregoing description, in accordance with one aspect of the subject matter herein, there is provided a blood processing system which includes a centrifuge assembly having a light-transmissive portion, a light reflector, and a fluid processing region at least partially positioned between the light-transmissive portion and the light reflector. The blood processing system also includes an optical sensor system configured to emit a scanning light beam along a path toward the light-transmissive portion of the centrifuge assembly. The light-transmissive portion of the centrifuge is configured to transmit at least a portion of the scanning light beam to the fluid processing region and the light reflector. The light reflector is configured to reflect at least a portion of the scanning light beam toward the optical sensor system along a path substantially coaxial to the path of the scanning light beam from the optical sensor system toward the light-transmissive portion of the centrifuge assembly.

In accordance with another aspect which may be used or combined with the preceding aspect, the path of the scanning light beam from the optical sensor system toward the light-transmissive portion of the centrifuge assembly is substantially parallel to a radius passing through the rotational axis of the centrifuge assembly. However, the path of the scanning light beam from the optical sensor system toward the light-transmissive portion of the centrifuge assembly is oriented so as not to pass through the rotational axis of the centrifuge assembly.

In accordance with another aspect which may be used or combined with any of the preceding aspects, the light reflector is a retroreflector.

In accordance with another aspect which may be used or combined with any of the preceding aspects, the optical sensor system also includes a first light detector, a source light configured to emit a source light beam, and a beam splitter. The beam splitter is configured to receive and split the source light beam into the scanning light beam and a reference light beam. The beam splitter also directs the scanning light beam toward the light-transmissive portion of the centrifuge assembly and directs the reference light beam toward the first light detector.

In accordance with another aspect which may be used or combined with the preceding aspect, the beam splitter is configured to direct the scanning light beam and the reference light beam in substantially perpendicular directions.

In accordance with another aspect which may be used or combined with any of the preceding two aspects, the optical sensor system further includes a second light detector. The beam splitter is configured to direct the reflected scanning light beam toward the second light detector.

In accordance with another aspect which may be used or combined with the preceding aspect, the beam splitter is configured to direct the reflected scanning light beam in a direction substantially perpendicular to the path of the scanning light beam from the light reflector toward the optical sensor system.

In accordance with another aspect which may be used or combined with any of the preceding four aspects, the optical sensor system further includes a controller associated with the first light detector and the source light and configured to adjust the brightness of the source light beam based at least in part on a characteristic of the reference light beam.

In accordance with another aspect which may be used or combined with any of the preceding aspects, the system is configured to determine the location of an interface between separated blood components in the centrifuge assembly.

In accordance with another aspect, there is provided a method for monitoring fluid within a blood processing system having a centrifuge assembly. The method includes separating blood in a centrifuge assembly into at least two blood components and directing a scanning light beam along a path toward and into the centrifuge assembly so as to intersect the blood or at least one of the blood components. At least a portion of the scanning light beam is reflected after intersecting the blood or blood component, with the reflected light being directed along a path out of the centrifuge assembly that is substantially coaxial to the path of the scanning light beam toward and into the centrifuge assembly. At least a portion of the reflected light is received and analyzed.

In accordance with another aspect which may be used or combined with the preceding aspect, the scanning light beam is directed in a direction that is substantially parallel to a radius passing through the rotational axis of the centrifuge assembly, but that does not pass through the rotational axis of the centrifuge assembly.

In accordance with another aspect which may be used or combined with any of the preceding two aspects, at least a portion of the scanning light beam is reflected with a retroreflector.

In accordance with another aspect which may be used or combined with any of the preceding three aspects, the reflected portion of the scanning light beam is directed in a direction substantially perpendicular to the path of the scanning light beam toward and into the centrifuge assembly prior to being received and analyzed.

In accordance with another aspect which may be used or combined with any of the preceding three aspects, a source light beam is split into the scanning light beam and reference light beam, with the reference light beam being directed toward a light detector substantially simultaneously with the scanning light beam being directed toward and into the centrifuge assembly.

In accordance with another aspect which may be used or combined with the preceding aspect, the scanning light beam and the reference light beam are directed in substantially perpendicular directions.

In accordance with another aspect which may be used or combined with any of the preceding two aspects, at least a portion of the reference light beam is received and analyzed, with the brightness of the source light beam being adjusted based at least in part on a characteristic of the reference light beam.

In accordance with another aspect which may be used or combined with any of the preceding seven aspects, the reflected light is analyzed to determine the location of an interface between separated blood components in the centrifuge assembly.

In accordance with another aspect, there is provided an optical sensor system for use in combination with a blood processing system. The optical sensor system includes a light source, a light detector, and an optical fiber providing a light path between the light source and the light detector.

In accordance with another aspect which may be used or combined with the preceding aspect, the light source is at least partially positioned within a housing, the light detector is positioned outside of the housing, and the optical fiber is connected to the housing.

In accordance with another aspect which may be used or combined with the preceding aspect, the optical fiber is adjustably connected to the housing.

In accordance with another aspect which may be used or combined with the preceding aspect, a plurality of optical fibers are connected to the housing by an adjustable module configured to simultaneously adjust the position of the optical fibers with respect to the housing.

In accordance with another aspect which may be used or combined with any of the preceding four aspects, a beam splitter is configured to receive light from the light source and direct at least a portion of the light toward the optical fiber.

In accordance with another aspect which may be used or combined with the preceding aspect, the beam splitter is configured to receive light from the light source and direct portions of the light toward a plurality of optical fibers in different directions.

In accordance with another aspect which may be used or combined with the preceding aspect, the beam splitter is configured to direct the portions of the light in opposite directions toward the optical fibers.

In accordance with another aspect which may be used or combined with any of the preceding seven aspects, the optical fiber is oriented at an angle with respect to the direction of a light beam emitted by the light source.

In accordance with another aspect which may be used or combined with any of the preceding eight aspects, the optical fiber is oriented substantially perpendicular to the direction of a light beam emitted by the light source.

In accordance with another aspect, there is provided a blood processing system which includes a centrifuge assembly having a light-transmissive portion, a light reflector, and a fluid processing region at least partially positioned between the light-transmissive portion and the light reflector. The blood processing system also includes an optical sensor system having a light source configured to emit a source light beam, a light detector, and an optical fiber providing a light path to the light detector. The light-transmissive portion of the centrifuge assembly is configured to transmit at least a portion of the source light beam to the fluid processing region and the light reflector. The light reflector is configured to reflect at least a portion of the source light beam toward the optical sensor assembly. The optical fiber is configured to conduct at least a portion of the reflected source light beam toward the light detector.

In accordance with another aspect which may be used or combined with the preceding aspect, the light source is at least partially positioned within a housing, the light detector is positioned outside of the housing, and the optical fiber is connected to the housing.

In accordance with another aspect which may be used or combined with the preceding aspect, the optical fiber is adjustable connected to the housing.

In accordance with another aspect which may be used or combined with the twenty-eighth aspect, a plurality of optical fibers connected to the housing by an adjustable module configured to simultaneously adjust the position of the optical fibers with respect to the housing.

In accordance with another aspect which may be used or combined with any of the preceding four aspects, a beam splitter is configured to receive the source light beam and direct at least a portion of the source light beam toward the optical fiber.

In accordance with another aspect which may be used or combined with the preceding aspect, the beam splitter is configured to direct a portion of the source light beam in a direction toward the optical fiber and to receive and direct at least a portion of the reflected source light beam toward another optical fiber in a different direction.

In accordance with another aspect which may be used or combined with the preceding aspect, the lights are directed toward the optical fibers in opposite directions.

In accordance with another aspect which may be used or combined with any of the preceding seven aspects, the optical fiber is oriented at an angle with respect to the direction of the source light beam.

In accordance with another aspect which may be used or combined with any of the preceding eight aspects, the optical fiber is oriented substantially perpendicular to the direction of the source light beam.

In accordance with another aspect, there is provided a method for monitoring fluid within a blood processing system having a centrifuge assembly. The method includes separating blood in a centrifuge assembly into at least two blood components and generating a source light beam. At least a portion of the source light beam is directed into the centrifuge assembly so as to intersect the blood or at least one of the blood components. At least a portion of the source light beam is reflected after intersecting the blood or blood component and is then directed toward a light detector through an optical fiber.

In accordance with another aspect which may be used or combined with the preceding aspect, at least one characteristic of the reflected source light beam is detected using the light detector and a characteristic of the blood or at least one of the blood components is determined based, at least in part, on a characteristic of the reflected source light beam.

In accordance with another aspect which may be used or combined with any of the preceding two aspects, the reflected source light beam is directed along a path substantially perpendicular to the direction of the reflected source light beam.

In accordance with another aspect which may be used or combined with any of the preceding three aspects, at least a portion of the source light beam is directed toward a second light detector through a second optical fiber.

In accordance with another aspect which may be used or combined with any of the preceding four aspects, the optical fiber is oriented at an angle with respect to the direction of the source light beam.

In accordance with another aspect which may be used or combined with any of the preceding five aspects, the optical fiber is oriented substantially perpendicular to the direction of the source light beam.

In accordance with another aspect, there is provided an optical sensor system for use in combination with a blood processing system. The optical sensor system includes a white light source.

In accordance with another aspect which may be used or combined with the preceding aspect, the white light source is a light-emitting diode.

In accordance with another aspect which may be used or combined with any of the preceding two aspects, the white light source has a relatively high spectral power distribution in the red wavelength spectrum.

In accordance with another aspect which may be used or combined with any of the preceding three aspects, the white light source has a relatively high spectral power distribution in the blue wavelength spectrum.

In accordance with another aspect which may be used or combined with any of the preceding four aspects, a light detector is positioned adjacent to the white light source and configured to monitor the intensity of light emitted by the white light source.

In accordance with another aspect, there is provided a blood processing system including a centrifuge assembly and an optical sensor system. The centrifuge assembly includes a light-transmissive portion and a fluid processing region positioned at least partially adjacent to the light-transmissive portion. The optical sensor system emits a white light directed toward the light-transmissive portion of the centrifuge assembly.

In accordance with another aspect which may be used or combined with the preceding aspect, the optical sensor system includes a white light source comprising a light-emitting diode.

In accordance with another aspect which may be used or combined with the preceding aspect, the white light source has a relatively high spectral power distribution in the red wavelength spectrum.

In accordance with another aspect which may be used or combined with any of the preceding two aspects, the white light source has a relatively high spectral power distribution in the blue wavelength spectrum.

In accordance with another aspect which may be used or combined with any of the preceding three aspects, a light detector is positioned adjacent to the white light source and configured to monitor the intensity of light emitted by the white light source.

According to another aspect, there is provided a method for monitoring fluid within a blood processing system having a centrifuge assembly. The method includes separating blood in a centrifuge assembly into at least two blood components and generating a source light beam comprising a white light. At least a portion of the source light beam is directed toward and into the centrifuge assembly so as to intersect the blood or at least one of the blood components. At least a portion of the source light beam is reflected after intersecting the blood or blood component and at least one characteristic of the reflected source light beam is detected.

In accordance with another aspect which may be used or combined with the preceding aspect, a characteristic of the blood or at least one of the blood components is determined based, at least in part, on a characteristic of the reflected source light beam.

In accordance with another aspect which may be used or combined with any of the preceding two aspects, the intensity of the source light beam is monitored from a location adjacent to the source of the source light beam.

In accordance with another aspect, there is provided a blood processing system which includes a centrifuge assembly having a light-transmissive portion, a light reflector, and a fluid processing region at least partially positioned between the light-transmissive portion and the light reflector. The blood processing system also includes an optical sensor system having a light source configured to emit a source light beam and a plurality of light detectors. The light-transmissive portion of the centrifuge assembly is configured to transmit at least a portion of the source light beam to the fluid processing region and the light reflector. The light reflector is configured to reflect at least a portion of the source light beam toward the optical sensor system. The plurality of light detectors are configured to detect at least one characteristic of the reflected source light beam at different locations.

In accordance with another aspect which may be used or combined with the preceding aspect, a plurality of optical fibers are configured to receive different portions of the reflected source light beam and to direct the different portions of the reflected source light beam to the light detectors.

In accordance with another aspect which may be used or combined with the preceding aspect, an adjustable module is configured to simultaneously adjust the position of the optical fibers with respect to the reflected source light beam.

In accordance with another aspect which may be used or combined with any of the preceding three aspects, the different locations are in the same plane.

In accordance with another aspect which may be used or combined with any of the preceding four aspects, the different locations are in a plane angled with respect to the rotational axis of the centrifuge assembly.

In accordance with another aspect, there is provided a method for monitoring fluid within a blood processing system having a centrifuge assembly. The method includes separating blood in a centrifuge assembly into at least two blood components and generating a source light beam. The source light beam is directed toward and into the centrifuge assembly so as to intersect the blood or at least one of the blood components. At least a portion of the source light beam is reflected after intersecting the blood or blood component and at least one characteristic of the reflected source light beam is detected at a plurality of different locations.

In accordance with another aspect which may be used or combined with the preceding aspect, a characteristic of the blood or at least one of the blood components is determined based, at least in part, on a characteristic of the reflected source light beam.

In accordance with another aspect which may be used or combined with any of the preceding two aspects, the different locations at which the characteristic of the reflected source light beam is detected are simultaneously adjusted.

In accordance with another aspect which may be used or combined with any of the preceding three aspects, the plurality of different locations are in the same plane.

In accordance with another aspect which may be used or combined with any of the preceding four aspects, the plurality of different locations are in a plane angled with respect to the rotational axis of the centrifuge assembly.

In accordance with another aspect, there is provided a blood processing system which includes a centrifuge assembly having a rotational axis. The blood processing system also includes an optical sensor system having a light source that emits a source light beam directed along a path parallel to a radius passing through the rotational axis of the centrifuge assembly. The path of the source light beam is oriented so as to not pass through the rotational axis of the centrifuge assembly.

In accordance with another aspect, there is provided a method for monitoring fluid within a blood processing system having a centrifuge assembly with a rotational axis. The method includes separating blood in a centrifuge assembly into at least two blood components and generating a source light beam. At least a portion of the source light beam is directed along a path parallel to a radius passing through the rotational axis of the centrifuge assembly, but oriented so as to not pass through the rotational axis of the centrifuge assembly, and into the centrifuge assembly so as to intersect the blood or at least one of the blood components. At least a portion of the source light beam is reflected after intersecting the blood or blood component and then at least one characteristic of the reflected source light beam is detected.

In accordance with another aspect which may be used or combined with the preceding aspect, a characteristic of the blood or at least one of the blood components is determined based, at least in part, on a characteristic of the reflected source light beam.

In accordance with another aspect, there is provided a blood processing system which includes a centrifuge assembly having a rotational axis. The centrifuge assembly has a light-transmissive portion, a fluid processing region positioned radially inwardly of the light-transmissive portion, and a yoke including a first support arm configured to rotate the light-transmissive portion and the fluid processing region about the rotational axis. The blood processing system also includes an optical sensor system configured to direct a light toward the light-transmissive portion of the centrifuge assembly. The yoke is positioned between the light-transmissive portion and the optical sensor system and is configured to allow passage of at least a portion of the light through the first support arm as the light is directed toward the light-transmissive portion.

In accordance with another aspect which may be used or combined with the preceding aspect, the first support arm defines a window through which light from the optical sensor system may pass.

In accordance with another aspect which may be used or combined with any of the preceding two aspects, the yoke includes a second support arm positioned opposite the first support arm.

In accordance with another aspect which may be used or combined with the preceding aspect, the angular extent of the window is at least as great as the angular extent of the second support arm.

In accordance with another aspect, there is provided a blood processing system which includes a centrifuge assembly having a rotational axis. The centrifuge assembly has a light-transmissive portion, a fluid processing region positioned radially inwardly of the light-transmissive portion, and a yoke. The yoke includes a first support arm configured to rotate the light-transmissive portion and the fluid processing region about the rotational axis. An optical fiber bundle extends between first and second ends and is associated with the support arm of the yoke. The blood processing system also includes an optical sensor system configured to direct a light toward the first end of the optical fiber bundle. The second end of the optical fiber bundle directs the light toward the light-transmissive portion.

In accordance with another aspect which may be used or combined with the preceding aspect, the optical sensor system is configured to direct the light in a direction substantially parallel to the rotational axis.

In accordance with another aspect which may be used or combined with any of the preceding two aspects, the second end of the optical fiber bundle is configured to direct the light in a generally radial direction.

In accordance with another aspect which may be used or combined with any of the preceding three aspects, the first end of the optical fiber bundle has a greater outer diameter than the second end.

In accordance with another aspect which may be used or combined with any of the preceding four aspects, a light reflector is associated with the light-transmissive portion. At least a portion of the light directed toward the light-transmissive portion is directed to the optical fiber bundle by the light reflector. The optical fiber bundle is configured to direct at least a portion of the reflected light toward the optical sensor system.

In accordance with another aspect which may be used or combined with the preceding aspect, the optical fiber bundle includes at least one signal fiber configured to direct reflected light from the light reflector toward the optical sensor system and a plurality of illumination fibers configured to direct light from the optical sensor system toward the light-transmissive portion. The at least one signal fiber is positioned directly adjacent to a central axis of the optical fiber bundle and the illumination fibers are positioned radially outwardly of the at least one signal fiber.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood processing system, comprising:
a centrifuge assembly including a light-transmissive portion and a fluid processing region positioned at least partially adjacent to the light-transmissive portion; and
an optical sensor system including
at least one light source,
a plurality of light detectors,
a spectral beam splitter, and
a controller, wherein
each light source of the optical sensor system comprises a white light source that emits only multiple-wavelength, true white light directed toward the light-transmissive portion of the centrifuge assembly, the spectral beam splitter is configured to receive at least a portion of the white light, separate said at least a portion of the white light into a plurality of lights having different wavelengths, and direct each one of the plurality of lights having different wavelengths to a different one of said plurality of light detectors, the plurality of light detectors are configured to transmit signals to the controller based, at least in part, on said plurality of lights having different wavelengths, and the controller is configured to simultaneously determine a plurality of characteristics of a fluid in the centrifuge assembly using the signals from the plurality of light detectors.

2. The blood processing system of claim 1, wherein the white light source comprises a light-emitting diode.

3. The blood processing system of claim 1, wherein the white light source has a relatively high spectral power distribution in a red wavelength spectrum.

4. The blood processing system of claim 1, wherein the white light source has a relatively high spectral power distribution in a blue wavelength spectrum.

5. The blood processing system of claim 1, further comprising a light detector positioned adjacent to the white light source and configured to monitor the intensity of light emitted by the white light source.

6. The blood processing system of claim 1, wherein the white light source comprises a laser diode.

7. The blood processing system of claim 1 wherein said plurality of characteristics includes at least two of lipid concentration, presence of cellular blood components, platelet concentration, and hemolysis.

* * * * *